US 9,901,359 B2

(12) United States Patent
Faller et al.

(10) Patent No.: US 9,901,359 B2
(45) Date of Patent: Feb. 27, 2018

(54) ACTUATION MECHANISM FOR USE WITH AN ULTRASONIC SURGICAL INSTRUMENT

(71) Applicant: Ethicon Endo-Surgery, Inc., Cincinnati, OH (US)

(72) Inventors: Craig N. Faller, Milford, OH (US); Kevin L. Houser, Springboro, OH (US); Mark A. Neurohr, Newport, KY (US)

(73) Assignee: Ethicon LLC, Guaynabo, PR (US)

( * ) Notice: Subject to any disclaimer, the term of this patent is extended or adjusted under 35 U.S.C. 154(b) by 107 days.

(21) Appl. No.: 14/269,546

(22) Filed: May 5, 2014

(65) Prior Publication Data

US 2014/0243863 A1  Aug. 28, 2014

Related U.S. Application Data

(60) Division of application No. 12/761,431, filed on Apr. 16, 2010, now Pat. No. 8,715,306, which is a division
(Continued)

(51) Int. Cl.
*A61B 17/29* (2006.01)
*A61B 17/32* (2006.01)
(Continued)

(52) U.S. Cl.
CPC .. *A61B 17/320092* (2013.01); *A61B 17/2909* (2013.01); *A61B 2017/00353* (2013.01);
(Continued)

(58) Field of Classification Search
CPC . A61B 17/28; A61B 17/29; A61B 17/320092; A61B 2017/00353;
(Continued)

(56) References Cited

U.S. PATENT DOCUMENTS 3,503,396 A  3/1970 Pierie et al.
3,503,397 A  3/1970 Fogarty et al.
(Continued)

FOREIGN PATENT DOCUMENTS

DE  4434938 C1  2/1996
JP  8-275950 A  10/1996
(Continued)

OTHER PUBLICATIONS

Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news-events/article20030224.html.
(Continued)

*Primary Examiner* — Michael Peffley
(74) *Attorney, Agent, or Firm* — Verne E. Kreger, Jr.

(57) ABSTRACT

An ultrasonic clamp coagulator assembly that is configured to permit selective cutting, coagulation and clamping of tissue during surgical procedures. An elongated portion of the instrument can be configured for endoscopic applications and has an outside diameter of less than 6 mm. The construction includes a clamping mechanism, including a clamp arm pivotally mounted at the distal portion of the instrument, which is specifically configured to create a desired level of tissue clamping forces, exceeding 4 pounds when the trigger is fully closed. The clamping mechanism includes a force-limiting mechanism that effectively smooths out abusive tissue forces.

8 Claims, 33 Drawing Sheets

Related U.S. Application Data of application No. 12/468,130, filed on May 19, 2009, now abandoned, which is a continuation of application No. 11/246,794, filed on Oct. 7, 2005, now Pat. No. 7,544,200.

(60) Provisional application No. 60/676,709, filed on May 2, 2005, provisional application No. 60/617,427, filed on Oct. 8, 2004.

(51) Int. Cl.
  *A61B 17/00* (2006.01)
  *A61B 17/28* (2006.01)

(52) U.S. Cl.
  CPC .............. *A61B 2017/00424* (2013.01); *A61B 2017/2825* (2013.01); *A61B 2017/2911* (2013.01); *Y10T 29/49005* (2015.01); *Y10T 29/49998* (2015.01)

(58) Field of Classification Search
  CPC ...... A61B 2017/2932; A61B 2017/294; A61B 2017/2825
  See application file for complete search history.

(56) References Cited

U.S. PATENT DOCUMENTS

| | | | |
|---|---|---|---|
| 4,663,677 A | 5/1987 | Griffith et al. | |
| D330,253 S | 10/1992 | Burek | |
| 5,322,055 A | 6/1994 | Davison et al. | |
| 5,323,055 A | 6/1994 | Yamazaki | |
| 5,358,506 A * | 10/1994 | Green | A61B 17/29 227/181.1 |
| 5,449,370 A | 9/1995 | Vaitekunas | |
| 5,607,436 A | 3/1997 | Pratt et al. | |
| 5,630,420 A | 5/1997 | Vaitekunas | |
| 5,782,834 A * | 7/1998 | Lucey | A61B 17/1608 604/22 |
| 5,873,873 A * | 2/1999 | Smith | A61B 17/320092 606/1 |
| 5,935,144 A | 8/1999 | Estabrook | |
| 5,938,633 A | 8/1999 | Beaupre | |
| 5,944,737 A | 8/1999 | Tsonton et al. | |
| 5,947,984 A | 9/1999 | Whipple | |
| 5,954,746 A | 9/1999 | Holthaus et al. | |
| 6,056,735 A | 5/2000 | Okada et al. | |
| 6,129,735 A | 10/2000 | Okada et al. | |
| 6,142,994 A | 11/2000 | Swanson et al. | |
| 6,165,191 A | 12/2000 | Shibata et al. | |
| 6,214,023 B1 | 4/2001 | Whipple et al. | |
| 6,254,623 B1 * | 7/2001 | Haibel, Jr. | A61B 17/320092 604/22 |
| 6,325,811 B1 * | 12/2001 | Messerly | A61B 17/320092 606/169 |
| 6,352,532 B1 | 3/2002 | Kramer et al. | |
| 6,425,907 B1 | 7/2002 | Shibata et al. | |
| 6,458,142 B1 | 10/2002 | Faller et al. | |
| 6,558,376 B2 | 5/2003 | Bishop | |
| 6,669,696 B2 | 12/2003 | Bacher et al. | |
| 6,676,660 B2 | 1/2004 | Wampler et al. | |
| 6,682,544 B2 | 1/2004 | Mastri et al. | |
| 6,945,981 B2 | 9/2005 | Donofrio et al. | |
| 6,958,070 B2 | 10/2005 | Witt et al. | |
| 7,101,371 B2 | 9/2006 | Dycus et al. | |
| 7,241,294 B2 | 7/2007 | Reschke | |
| 7,544,200 B2 | 6/2009 | Houser | |
| 7,717,915 B2 | 5/2010 | Miyazawa | |
| 7,846,155 B2 | 12/2010 | Houser et al. | |
| 8,057,467 B2 | 11/2011 | Faller et al. | |
| 8,715,306 B2 | 5/2014 | Faller et al. | |
| 2002/0019646 A1 | 2/2002 | Mastri et al. | |
| 2002/0052595 A1 | 5/2002 | Witt et al. | |
| 2002/0123742 A1 * | 9/2002 | Baxter | A61B 17/2909 606/1 |
| 2003/0004507 A1 | 1/2003 | Francischelli et al. | |
| 2003/0093113 A1 | 5/2003 | Fogarty et al. | |
| 2003/0114874 A1 | 6/2003 | Craig et al. | |
| 2005/0033337 A1 | 2/2005 | Muir et al. | |
| 2005/0143759 A1 | 6/2005 | Kelly | |
| 2005/0192610 A1 | 9/2005 | Houser et al. | |
| 2006/0079874 A1 | 4/2006 | Faller et al. | |
| 2006/0079875 A1 | 4/2006 | Faller | |
| 2006/0079876 A1 | 4/2006 | Houser et al. | |
| 2006/0079877 A1 | 4/2006 | Houser et al. | |
| 2006/0079879 A1 | 4/2006 | Faller et al. | |

FOREIGN PATENT DOCUMENTS

| | | |
|---|---|---|
| JP | 10-5236 A | 1/1998 |
| JP | 2000-139943 A | 5/2000 |
| JP | 2003-510158 A | 3/2003 |
| JP | 2004-209043 A | 7/2004 |
| WO | WO 00/24322 A1 | 5/2000 |
| WO | WO 02/080799 A1 | 10/2002 |
| WO | WO 2005/084250 A2 | 9/2005 |

OTHER PUBLICATIONS

International Search Report dated Nov. 30, 2006 International Application No. PCT/US2005/36389.

European Search Report dated Jan. 11, 2010, Application No. 05818040.7.

\* cited by examiner

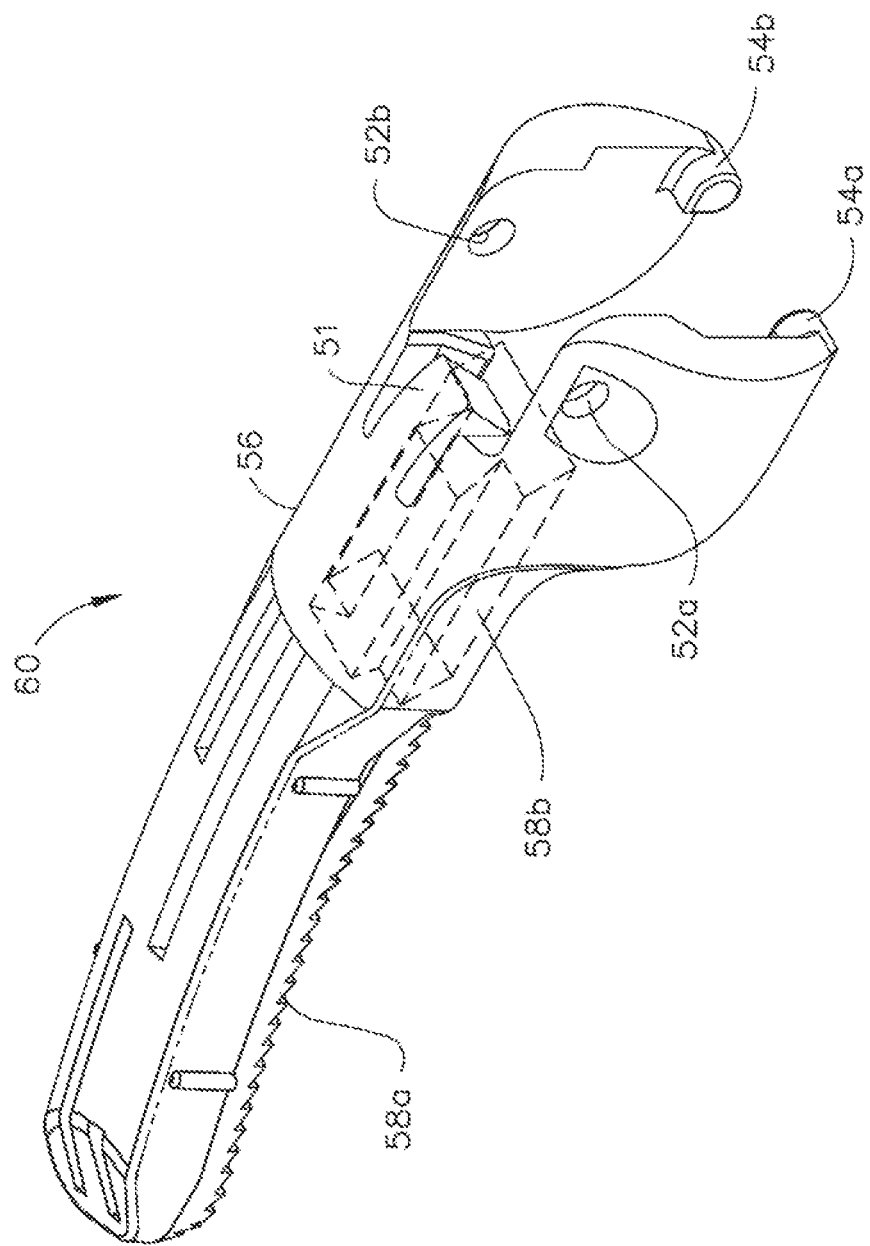

ACTUATION MECHANISM FOR USE WITH AN ULTRASONIC SURGICAL INSTRUMENT

REFERENCE TO RELATED APPLICATIONS

The present application is a divisional of U.S. patent application Ser. No. 12/761,431, filed on Apr. 16, 2010, now U.S. Pat. No. 8,715,306, which is a divisional of U.S. patent application Ser. No. 12/468,130, filed on May 19, 2009, abandoned, which is a continuation of U.S. Pat. No. 7,544,200, which claims the priority benefit of U.S. provisional patent application Ser. Nos. 60/617,427, filed on Oct. 8, 2004, and 60/676,709, filed on May 2, 2005, all of which are incorporated herein by reference.

This application contains subject matter that relates to and incorporates by reference in their entirety, for any and all purposes, the following non-provisional applications:

TISSUE PAD FOR USE WITH AN ULTRASONIC SURGICAL INSTRUMENT, Ser. No. Ser. No. 11/245,819, abandoned;

COMBINATION TISSUE PAD FOR USE WITH AN ULTRASONIC SURGICAL INSTRUMENT, Ser. No. 11/246,794, filed Oct. 7, 2005, now U.S. Pat. No. 7,544,200;

ACTUATION MECHANISM FOR USE WITH AN ULTRASONIC SURGICAL INSTRUMENT, Ser. No. 11/246,826, filed Oct. 7, 2005, abandoned;

CLAMP MECHANISM FOR USE WITH AN ULTRASONIC SURGICAL INSTRUMENT, Ser. No. 11/246,264, filed Oct. 7, 2005, now U.S. Pat. No. 8,057,467;

FEEDBACK MECHANISM FOR USE WITH AN ULTRASONIC SURGICAL INSTRUMENT, Ser. No. 11/246,384, filed Oct. 7, 2005, abandoned;

HANDLE ASSEMBLY HAVING HAND ACTIVATION FOR USE WITH AN ULTRASONIC SURGICAL INSTRUMENT, Ser. No. 11/246,330, filed Oct. 7, 2005, now U.S. Pat. No. 7,846,155;

ULTRASONIC SURGICAL SHEARS AND TISSUE PAD FOR SAME, Ser. No. 11/065,378, filed Feb. 24, 2005, abandoned; and HAND ACTIVATED ULTRASONIC INSTRUMENT, Ser. No. 10/869,351, filed Jun. 16, 2004.

FIELD OF THE INVENTION

The present invention relates, in general, to ultrasonic surgical instruments and, more particularly, to an ultrasonic surgical clamp coagulator apparatus particularly configured to provide increased tissue transaction forces.

BACKGROUND OF THE INVENTION

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and homeostasis by coagulation, desirably minimizing patient trauma. The cutting action is typically effected by an end-effector at the distal end of the instrument, which transmits ultrasonic energy to tissue brought into contact with the end-effector. Ultrasonic instruments of this nature can be configured for open surgical use, laparoscopic or endoscopic surgical procedures including robotic-assisted procedures.

Ultrasonic surgical instruments have been developed that include a clamp mechanism to press tissue against the blade of the end-effector in order to couple ultrasonic energy to the tissue of a patient. Such an arrangement (sometimes referred to as a clamp coagulator shears or an ultrasonic transector) is disclosed in U.S. Pat. Nos. 5,322,055; 5,873,873 and 6,325,811, all of which are incorporated herein by reference. The surgeon activates the clamp arm to press the clamp pad against the blade by squeezing on the handgrip or handle.

Some current ultrasonic shears devices, however, have the tendency to create tissue tags. Tissue tags are the tissue that remains clamped in the jaw that is not transected after the majority of the tissue in the jaw has been transected and falls away. Tissue tags may result from insufficient end-effector proximal loading and/or lower proximal blade activity. Surgeons may mitigate tissue tags either through the addition of vertical tension (i.e. putting tension on the tissue using the blade) or rearward traction on the device in order to move the untransected tissue to a more active portion of the blade to complete the cut.

Some current ultrasonic shears devices utilize tissue pads that close in parallel with the surface of the blade. This presents certain problems in terms of the pressure profile exerted on the tissue. As tissue is compressed between the jaw and the blade, the proximal portion of the blade deflects under load more than the proximal portion of the clamp arm moves in applying the load against the blade. This deflection is in part created by the portion of the blade distal to the most distal node of the device. It is also partly created by the deflection of the transmission rod proximal to the most distal node. Additionally, the fact that blade amplitude decreases moving proximal of the tip of the blade makes the situation worse since the amount of energy transferred to the tissue, even if the pressure was constant, is reduced.

Current tissue pad designs utilize PTFE material to contact the tissue and blade. Although these designs have been adequate, they tend to suffer from longevity issues since the pads tend to deteriorate over long surgical procedures. Additionally, newer designs of clamp coagulator shears increase blade amplitude and/or the loading of the pad against the tissue and blade and overwhelm the pad material, resulting in less than required tissue pad life. The pad material limits the amount of force that may be applied against the tissue and blade, which in turn limits the tissue thickness or vessel size that some current clamp coagulator shears may effectively cut and coagulate.

Some current designs of clamp coagulator shears utilize an inner tube within an outer tube concept to drive the clamp arm open and close. During surgical procedures the clamp arm may be subjected to axial clamp forces exceeding 2.5 pounds and/or torsional abuse loads and may cause the clamp arm to disengage from the inner tube or completely from the shears.

Some current designs of clamp coagulator shears utilize a constant force spring mechanism that prevents the application of too much force to the clamp arm and blade. Although the mechanism provides relatively constant force to the system, the spring imparts some slope to the force curve. In applications where the clamp force is low, the slope is not significant. In applications with high clamp forces, however, the difference in force attributable to the slope over the possible range of spring compressions becomes very significant and may exceed the maximum force allowable in the blade, in the tube assemblies or in other components of the system. The high slope could allow the maximum force to be exceeded under abuse modes or through normal manufacturing tolerance variations. If this occurs the blade may bend, the actuation mechanism may fail or undesirable tissue effects may occur (i.e. fast cutting, but minimal tissue coagulation). This situation is aggravated by the fact that the jaw (the clamp arm and pad) of the device can meet sufficient resistance to engage the force limiting mechanism when the jaw almost contacts the blade (when transecting thin tissue or at the end of the transaction or clamping solid objects such as other devices) or when the jaw is still open (when transecting thick tissue).

Some current designs of clamp coagulator shears utilize force-limiting springs to ensure that clamp forces are within a specified range. It is also necessary for the force-limiting spring design to allow the surgeon to "feather" (apply less than the maximum force and slowly increase to the maximum force). In these mechanisms, therefore, the jaws close until a predetermined force is met and then the additional stroke drives the mechanism into the force limiting range. In some cases, though, the surgeon may, unknowingly, fail to apply the full force of the jaw against the tissue resulting in incomplete tissue cuts or insufficient coagulation. Alternatively, the surgeon may unknowingly release full force of the jaw against the tissue during a transaction that results in incomplete tissue cuts or insufficient coagulation.

Some current designs of clamp coagulator shears utilize a foot pedal to energize the surgical instrument. The surgeon operates the foot pedal while simultaneously applying pressure to the handle to press tissue between the jaw and blade to activate a generator that provides energy that is transmitted to the cutting blade for cutting and coagulating tissue. Key drawbacks with this type of instrument activation include the loss of focus on the surgical field while the surgeon searches for the foot pedal, the foot pedal getting in the way of the surgeon's movement during a procedure and surgeon leg fatigue during long cases.

Some current designs of clamp coagulator shears have eliminated the foot pedal and provided hand activation on a stationary trigger. This may be cumbersome, especially for surgeons with large hands.

Some current designs of clamp coagulator utilize handles that are either of a pistol or scissors grips design. The scissor grip designs may have one thumb or finger grip that is immovable and fixed to the housing and one movable thumb or finger grip. This type of grip may not be entirely familiar to surgeons who use other open-type surgical instruments, such as hemostats, where both thumb and finger grips move in opposition to one another.

It would be desirable to provide an ultrasonic surgical instrument that overcomes some of the deficiencies of current instruments. The ultrasonic surgical instrument described herein overcomes those deficiencies.

BRIEF SUMMARY OF THE INVENTION

An ultrasonic clamp coagulator assembly embodying the principles of the present invention is configured to permit selective cutting, coagulation and clamping of tissue during surgical procedures. An elongated portion of the instrument can be configured for endoscopic applications and has an outside diameter of less than 6 mm. The construction includes a clamping mechanism, including a clamp arm pivotally mounted at the distal portion of the instrument, which is specifically configured to create a desired level of tissue clamping forces, exceeding 4 pounds when the trigger is fully closed, notwithstanding the relatively small cross-section of the elongated portion.

The clamping mechanism also includes a pad design and pad material that enables the higher tissue clamping forces.

The clamp coagulator device also includes a force-limiting mechanism that effectively smooths out abusive tissue forces.

The clamp coagulator device also features hand activation configured in such a way to provide an ergonomically pleasing grip and operation for the surgeon. Hand switches are be placed in the range of the natural swing of the surgeon's thumb, whether gripping surgical instrument right-handed or left handed.

BRIEF DESCRIPTION OF THE FIGURES

The novel features of the invention are set forth with particularity in the appended claims. The invention itself, however, both as to organization and methods of operation, may best be understood by reference to the following description, taken in conjunction with the accompanying drawings in which:

FIG. 3d is a perspective view of the tissue pads aligned and staked within the clamp arm;

DETAILED DESCRIPTION OF THE INVENTION

Figure 1:
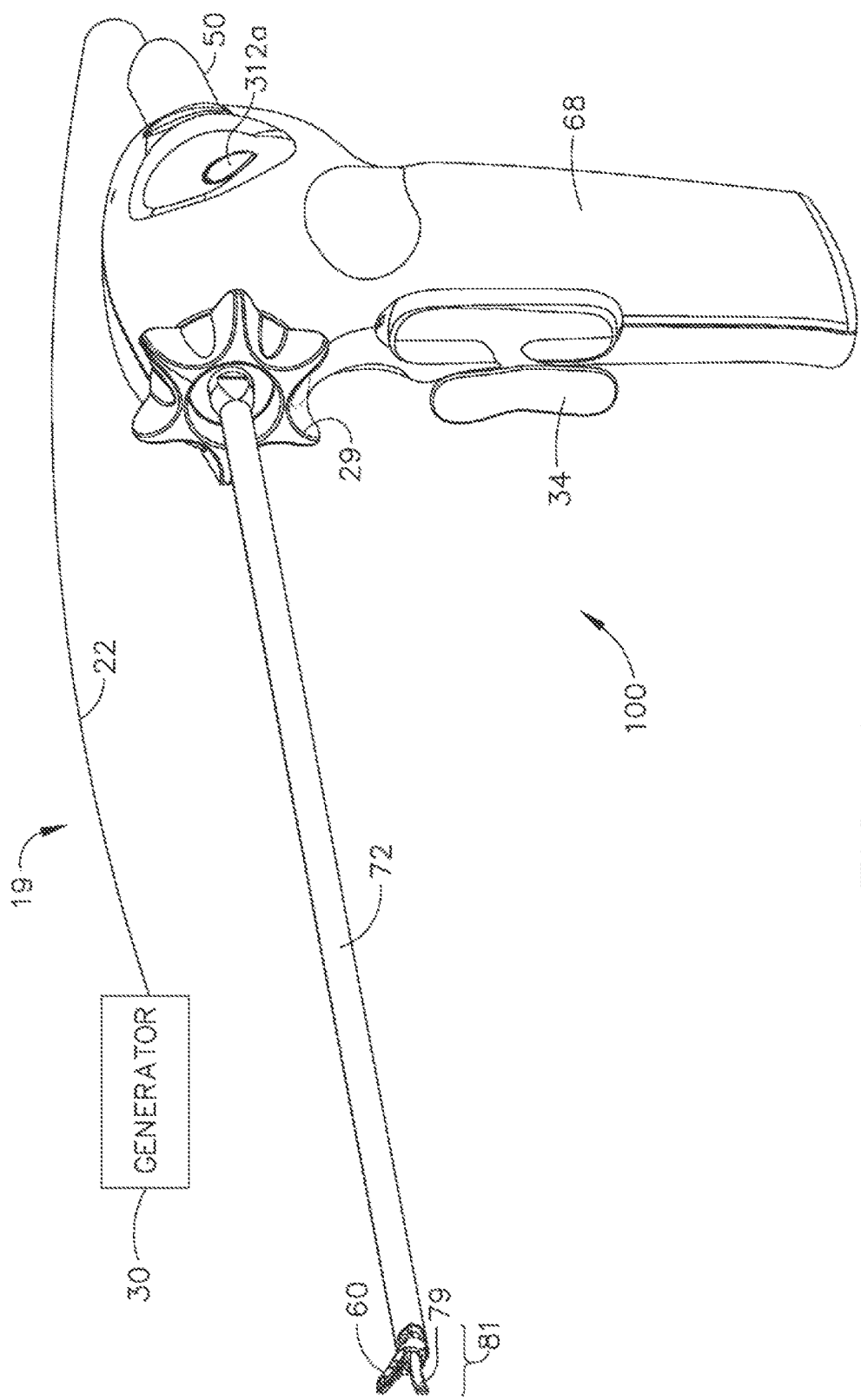
FIG. 1 is a perspective view illustrating an embodiment of an ultrasonic surgical instrument in accordance with the present invention.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Further, unless otherwise indicated, the terms and expressions employed herein have been chosen for the purpose of describing the illustrative embodiments of the present invention for the convenience of the reader and are not for the purpose of limiting the invention.

Further, it is understood that any one or more of the following-described embodiments, expressions of embodiments, examples, etc. can be combined with any one or more of the other following-described embodiments, expressions of embodiments, examples, etc.

The present invention is particularly directed to an improved ultrasonic surgical clamp coagulator apparatus which is configured for effecting tissue cutting, coagulation, and/or clamping during surgical procedures. The present apparatus can be readily configured for use in open surgical procedures, as well as laparoscopic or endoscopic procedures and robot-assisted surgical procedures. Versatile use is facilitated by selective use of ultrasonic energy. When ultrasonic components of the apparatus are inactive, tissue can be readily gripped and manipulated, as desired, without tissue cutting or damage. When the ultrasonic components are activated, the apparatus permits tissue to be gripped for coupling with the ultrasonic energy to effect tissue coagulation, with application of increased pressure efficiently effecting tissue cutting and coagulation. If desired, ultrasonic energy can be applied to tissue without use of the clamping mechanism of the apparatus by appropriate manipulation of the ultrasonic blade.

As will become apparent from the following description, the present clamp coagulator apparatus is particularly configured for disposable use by virtue of its straightforward construction. As such, it is contemplated that the apparatus be used in association with an ultrasonic generator unit of a surgical system, whereby ultrasonic energy from the generator unit provides the desired ultrasonic actuation for the present clamp coagulator apparatus. It will be appreciated that a clamp coagulator apparatus embodying the principles of the present invention can be configured for non-disposable or multiple use, and non-detachably integrated with an associated ultrasonic generator unit. However, detachable connection of the present clamp coagulator apparatus with an associated ultrasonic generator unit is presently preferred for single-patient use of the apparatus.

The present invention will be described in combination with an ultrasonic instrument as described herein. Such description is exemplary only, and is not intended to limit the scope and applications of the invention. For example, the invention is useful in combination with a multitude of ultrasonic instruments including those described in, for example, U.S. Pat. Nos. 5,938,633; 5,935,144; 5,944,737; 5,322,055, 5,630,420; and 5,449,370.

Figure 2:
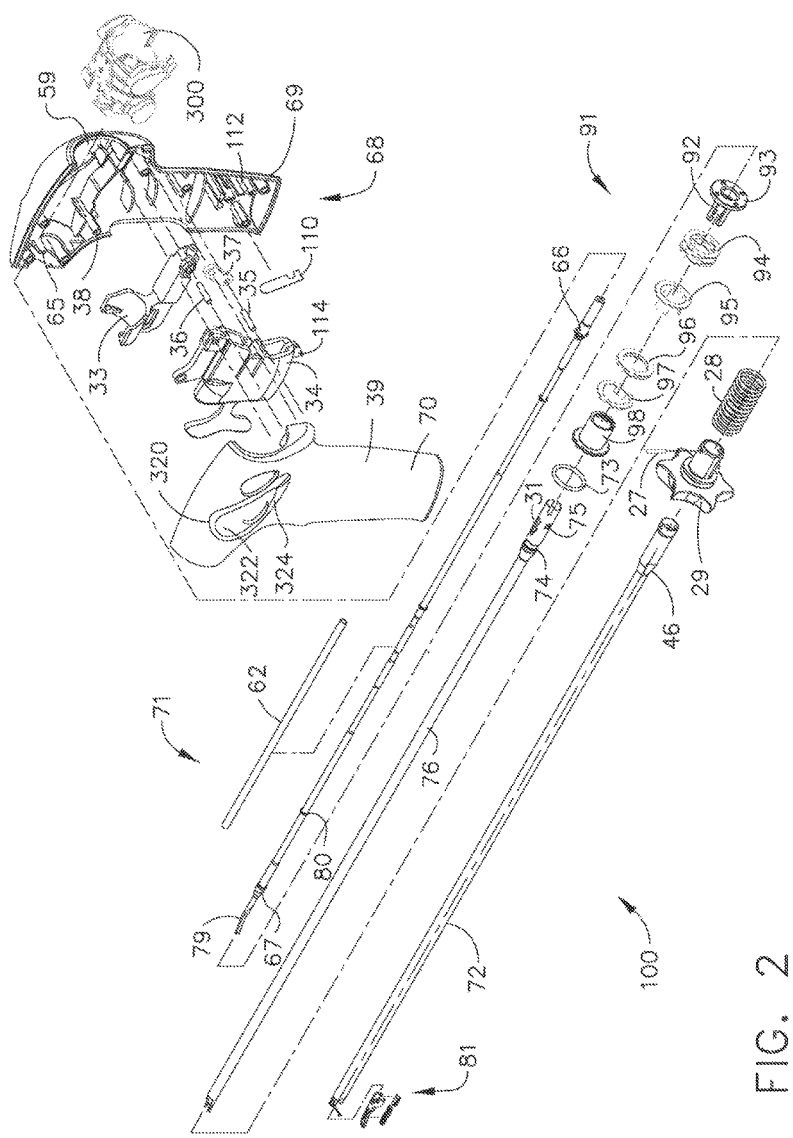
FIG. 2 is a perspective assembly view of an embodiment of an ultrasonic surgical instrument in accordance with the present invention.

With reference to FIGS. 1-3, an embodiment of a surgical system 19, including an ultrasonic surgical instrument 100 in accordance with the present invention is illustrated. The surgical system 19 includes an ultrasonic generator 30 connected to an ultrasonic transducer 50 via cable 22, and an ultrasonic surgical instrument 100. It will be noted that, in some applications, the ultrasonic transducer 50 is referred to as a "hand piece assembly" because the surgical instrument of the surgical system 19 is configured such that a surgeon may grasp and manipulate the ultrasonic transducer 50 during various procedures and operations. A suitable generator is the GEN 300 sold by Ethicon Endo-Surgery, Inc. of Cincinnati, Ohio.

The ultrasonic surgical instrument 100 includes a multi-piece handle assembly 68 adapted to isolate the operator from the vibrations of the acoustic assembly contained within transducer 50. The handle assembly 68 can be shaped to be held by a user in a conventional manner, but it is contemplated that the present ultrasonic surgical instrument 100 principally be grasped and manipulated by a trigger-like arrangement provided by a handle assembly of the instrument, as will be described. While multi-piece handle assembly 68 is illustrated, the handle assembly 68 may comprise a single or unitary component. The proximal end of the ultrasonic surgical instrument 100 receives and is fitted to the distal end of the ultrasonic transducer 50 by insertion of the transducer into the handle assembly 68. The ultrasonic surgical instrument 100 may be attached to and removed from the ultrasonic transducer 50 as a unit. The ultrasonic surgical instrument 100 may include a handle assembly 68, comprising mating housing portion 69, housing portion 70, and a transmission assembly 71. When the present instrument is configured for endoscopic use, the construction can be dimensioned such that transmission assembly 71 has an outside diameter of approximately 5.5 mm. The elongated transmission assembly 71 of the ultrasonic surgical instrument 100 extends orthogonally from the instrument handle assembly 68. The transmission assembly 71 can be selectively rotated with respect to the handle assembly 68 as further described below. The handle assembly 68 may be constructed from a durable plastic, such as polycarbonate or a liquid crystal polymer. It is also contemplated that the handle assembly 68 may alternatively be made from a variety of materials including other plastics, ceramics or metals.

The transmission assembly 71 may include an outer tubular member or outer sheath 72, an inner tubular actuating member 76, a waveguide 80 and end-effector 81 (blade 79, clamp arm 56 and one or more clamp pads 58). As will be described, the outer sheath 72, the actuating member 76, and the waveguide or transmission rod 80 may be joined together for rotation as a unit (together with ultrasonic transducer 50) relative to handle assembly 68. The waveguide 80, which is adapted to transmit ultrasonic energy from transducer 50 to blade 79 may be flexible, semi-flexible or rigid. The waveguide 80 may also be configured to amplify the mechanical vibrations transmitted through the waveguide 80 to the blade 79 as is well known in the art. The waveguide 80 may further have features to control the gain of the longitudinal vibration along the waveguide 80 and features to tune the waveguide 80 to the resonant frequency of the system. In particular, waveguide 80 may have any suitable cross-sectional dimension. For example, the waveguide 80 may have a substantially uniform cross-section or the waveguide 80 may be tapered at various sections or may be tapered along its entire length. In one expression of the current embodiment, the waveguide diameter is about 0.113 inches nominal to minimize the amount of deflection at the blade 79 so that gapping in the proximal portion of the end effector 81 is minimized.

Ultrasonic waveguide 80 may further include at least one radial hole or aperture 66 extending there through, substantially perpendicular to the longitudinal axis of the waveguide 80. The aperture 66, which may be positioned at a node, is configured to receive a connector pin 27 which connects the waveguide 80, to the tubular actuating member 76, and the tubular outer sheath 72, a rotation knob 29 together for conjoint rotation, including the end effector 81, relative to instrument handle assembly 68.

In one embodiment of the present invention, the ultrasonic waveguide 80 may have a plurality of grooves or notches (not shown) formed in its outer circumference. The grooves may be located at nodes of the waveguide 80 to act as alignment indicators for the installation of a damping sheath 62 and stabilizing silicone rings or compliant supports during manufacturing. A seal 67 may be provided at the distal-most node, nearest the end-effector 81, to abate passage of tissue, blood, and other material in the region between the waveguide 80 and actuating member 76.

The blade 79 may be integral with the waveguide 80 and formed as a single unit. In an alternate expression of the current embodiment, blade 79 may be connected by a threaded connection, a welded joint, or other coupling mechanisms. The distal end of the blade 79 is disposed near an anti-node in order to tune the acoustic assembly to a preferred resonant frequency fo when the acoustic assembly is not loaded by tissue. When ultrasonic transducer 50 is energized, the distal end of blade 79 is configured to move longitudinally in the range of, for example, approximately 10 to 500 microns peak-to-peak, and preferably in the range of about 20 to about 200 microns at a predetermined vibrational frequency fo of, for example, 55,500 Hz.

In accordance with the illustrated embodiment, blade 79 is curved along with the associated clamp arm 56. This is illustrative only, and blade 79 and a corresponding clamp arm 56 may be of any shape as is known to the skilled artisan.

Ultrasonic transducer 50, and an ultrasonic waveguide 80 together provide an acoustic assembly of the present surgical system 19, with the acoustic assembly providing ultrasonic energy for surgical procedures when powered by generator 30. The acoustic assembly of surgical instrument 100 generally includes a first acoustic portion and a second acoustic portion. In the present embodiment, the first acoustic portion comprises the ultrasonically active portions of ultrasonic transducer 50, and the second acoustic portion comprises the ultrasonically active portions of transmission assembly 71. Further, in the present embodiment, the distal end of the first acoustic portion is operatively coupled to the proximal end of the second acoustic portion by, for example, a threaded connection.

With particular reference to FIGS. 2, and 9-11, reciprocal movement of actuating member 76 drives the clamp arm open and closed. A force-limiting mechanism 91 is operatively connected to actuating member 76 and comprises a tube collar cap 98 that secures distal washer 97, distal wave spring 96, proximal washer 95 and proximal wave spring 94 onto collar cap 93. Collar 93 includes axially extending lugs 92 in engagement with suitable openings 75 in the proximal portion of tubular actuating member 76. A circumferential groove 74 on the actuating member 76 receives on O-ring 73 for engagement with the inside surface of outer sheath 72.

Rotation of the actuating member 76 together with tubular outer sheath 72 and inner waveguide 80 is provided by a connector pin 27 extending through these components and rotation knob 29. Tubular actuating member 76 includes an elongated slot 31 through which the connector pin 27 extends to accommodate reciprocal movement of the actuating member 76 relative to the outer sheath 72 and inner waveguide 80.

The force limiting mechanism 91 provides a portion of the clamp drive mechanism of the instrument 100, which affects pivotal movement of the clamp arm 56 by reciprocation of actuating member 76. The clamp drive mechanism further includes a drive yoke 33 which is operatively connected with an operating trigger 34 of the instrument, with the operating trigger 34 thus interconnected with the reciprocable actuating member 76 via drive yoke 33 and force limiting mechanism 91. Trigger 34 is rotatably connected to drive yoke 33 via pins 35 and 36 and link 37 and rotatably connected to drive yoke 33 and housing 68 via post 38.

Movement of trigger 34 toward handgrip 68 translates actuating member 76 proximally, thereby pivoting clamp arm 56 toward blade 79. The trigger-like action provided by trigger 34 and cooperating handgrip 68 facilitates convenient and efficient manipulation and positioning of the instrument, and operation of the clamping mechanism at the distal portion of the instrument whereby tissue is efficiently urged against the blade 79. Movement of trigger 34 away from handgrip 68 translates actuating member 76 distally, thereby pivoting clamp arm 56 away from blade 79.

With particular reference to FIGS. 1-4, therein is illustrated one embodiment of clamp member 60 for use with the present ultrasonic surgical instrument 100 and which is configured for cooperative action with blade 79. The clamp member 60 in combination with blade 79 is commonly referred to as the end effector 81, and the clamp member 60 is also commonly referred to as the jaw. The clamp member 60 includes a pivotally movable clamp arm 56, which is connected to the distal end of outer sheath 72 and actuation member 76, in combination with a tissue engaging pad or clamp pad 58. In one expression of the embodiment, clamp pad 58 is formed from TEFLON® trademark name of E. I. Du Pont de Nemours and Company, a low coefficient of friction polymer material, or any other suitable low-friction material. Clamp pad 58 mounts on the clamp arm 56 for cooperation with blade 79, with pivotal movement of the clamp arm 56 positioning the clamp pad in substantially parallel relationship to, and in contact with, blade 79, thereby defining a tissue treatment region. By this construction, tissue is grasped between clamp pad 58 and blade 79. As illustrated, clamp pad 58 may be provided with non-smooth surface, such as a saw tooth-like configuration to enhance the gripping of tissue in cooperation with the blade 79. The saw tooth-like configuration, or teeth, provide traction against the movement of the blade. The teeth also provide counter traction to the blade and clamping movement. As would be appreciated by one skilled in the art, the saw tooth-like configuration is just one example of many tissue engaging surfaces to prevent movement of the tissue relative to the movement of the blade 79. Other illustrative examples include bumps, criss-cross patterns, tread patterns, a bead or sand blasted surface, etc.

Figure 3A:
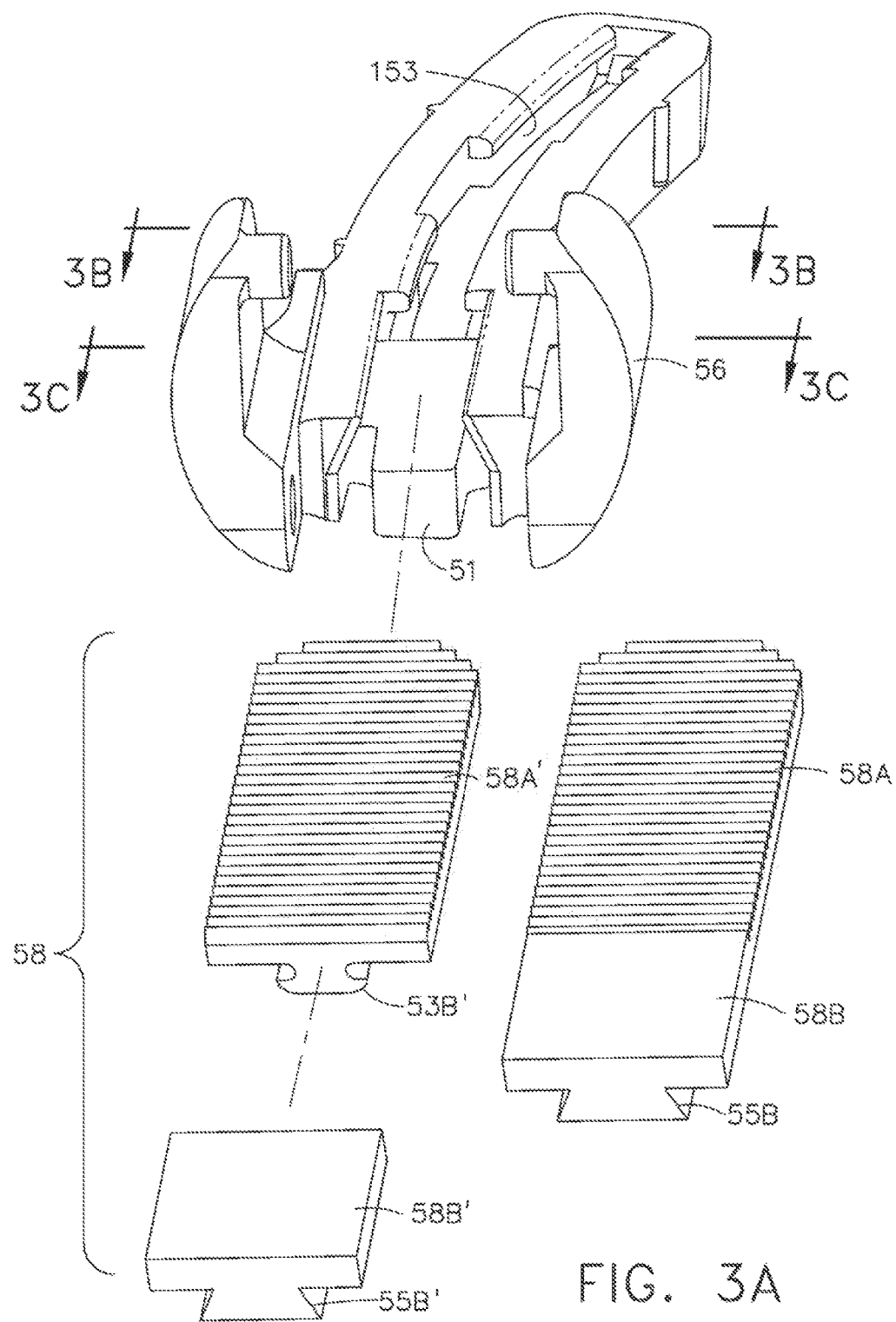
FIG. 3a is a perspective assembly view of the clamp arm and tissue pads.
Figure 3B:
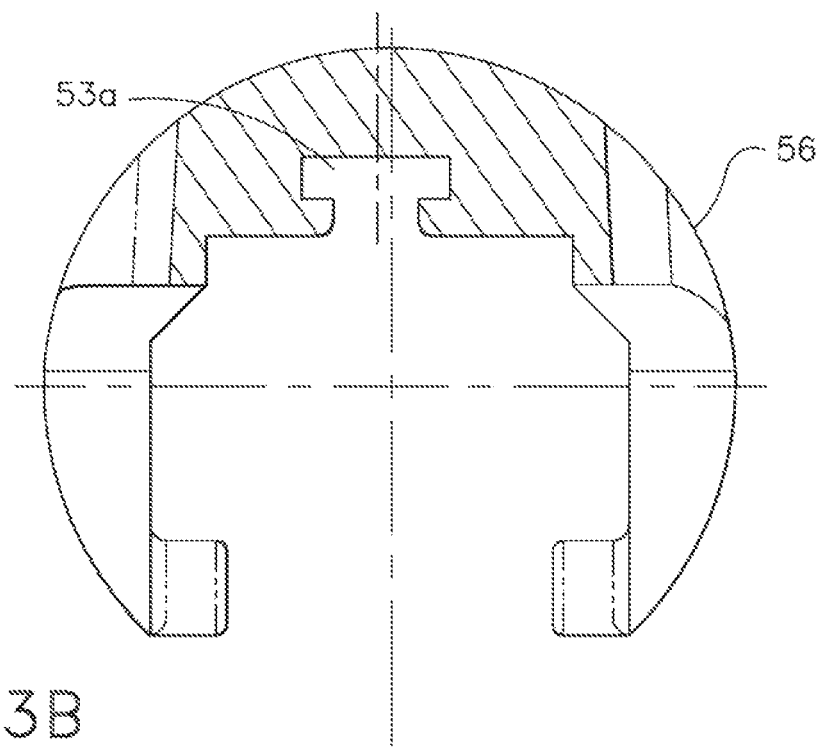
FIG. 3b is an elevation section view of the clamp arm and "T" groove.
Figure 3C:
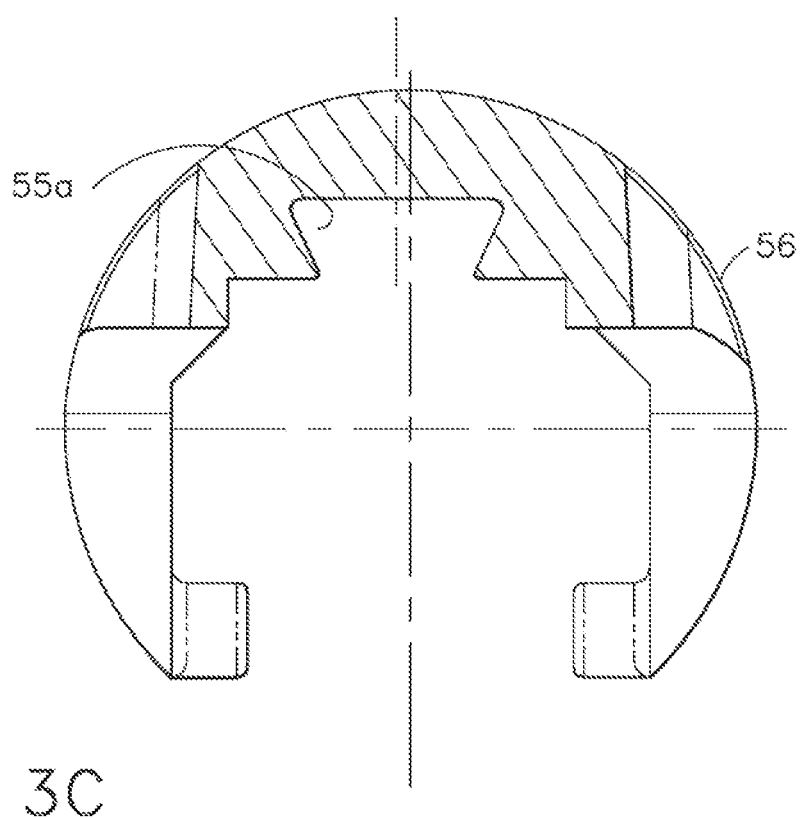
FIG. 3c is an elevation section view of the clamp arm and dovetail groove.
Figure 3F:
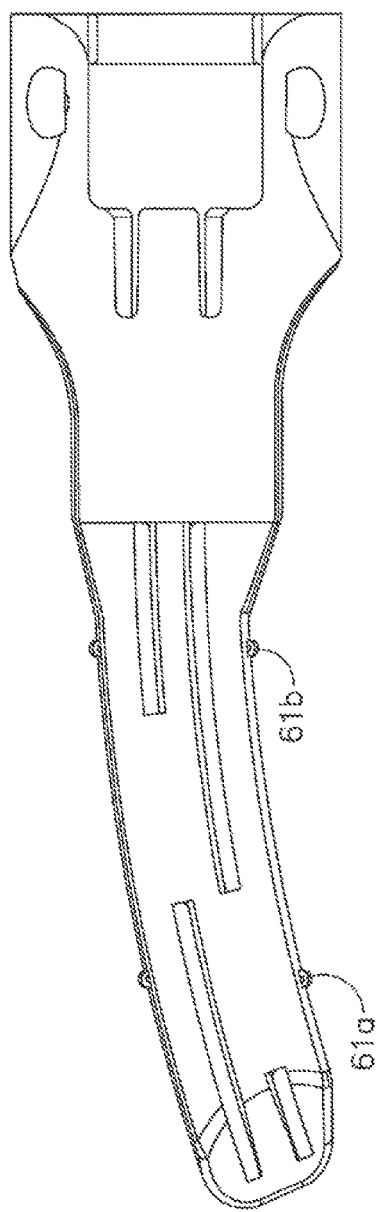
FIG. 3f is a top plan view of the clamp arm.
Figure 3E:
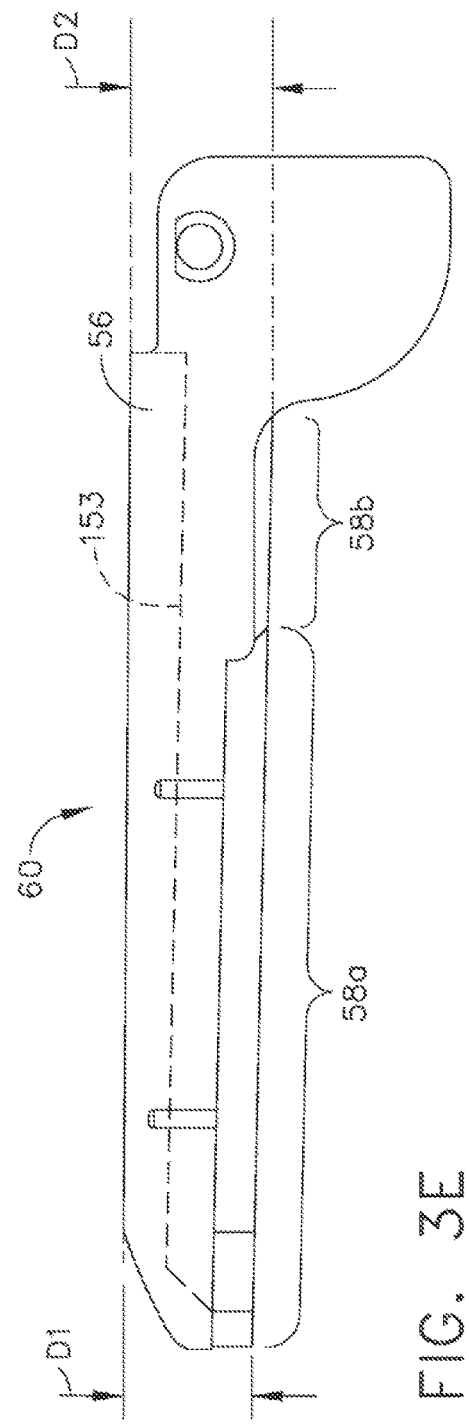
FIG. 3e is an elevation view of the clamp arm illustrating the tapered profile.

With particular reference to FIG. 3a, a first expression of the current embodiment includes a clamp pad 58 having a proximal portion 58b that is smoother than a distal portion 58a, such that proximal portion 58b may be devoid of saw-tooth-like teeth or other tissue engaging surfaces contemplated. Utilizing a smooth proximal portion 58b on clamp pad 58 allows tissue in the proximal region to move distally, following the vibratory motion of the blade, to the more active region of the blade 79 to prevent tissue tagging. This concept takes advantage of the inherent motion profile of blade 79. Due to sinusoidal motion, the greatest displacement or amplitude of motion is located at the most distal portion of blade 79, while the proximal portion of the tissue treatment region is on the order of 50% of the distal tip amplitude. During operation, the tissue in the proximal region of end effector (area of portion 58b) will desiccate and thin, and the distal portion of end effector 81 will transect tissue in that distal region, thereby allowing the desiccated and thin tissue within the proximal region to slide distally into the more active region of end effector 81 to complete the tissue transaction.

In a second expression of the current embodiment, clamp pad 58 consists of one single pad having a smooth proximal end 58b and a distal portion 58a that comprises a saw tooth-like configuration. In a third expression of the current embodiment, clamp pad 58 may consist of two separate components, distal portion 58a' that comprises saw tooth-like teeth and proximal portion 58b' that is smoother relative to distal portion 58a'. The advantage of two separate components 58a' and 58b' is that each pad may be constructed from different materials. For example, having a two-piece tissue pad allows the use of a very lubricious material at the distal end that is not particularly resistant to high temperatures compared to a very high temperature material at the proximal end that is not particularly lubricious because the proximal end is an area of lower amplitude. Such a configuration matches the tissue pad materials to the amplitude of the blade 79.

In a fourth expression of the current embodiment of the present invention, clamp pad 58a' is formed from TEFLON® or any other suitable low-friction material. Clamp pad 58b' is formed from a base material and at least one filler material, which is a different material from the base material. The surface of proximal clamp pad 58b' may be smoother than distal clamp pad 58a', or proximal clamp pad 58b' may also have a similar type saw-tooth configuration.

Several benefits and advantages are obtained from one or more of the expressions of the invention. Having a tissue pad with a base material and at-least-one filler material allows the base material and the at-least-one filler material to be chosen with a different hardness, stiffness, lubricity, dynamic coefficient of friction, heat transfer coefficient, abradability, heat deflection temperature, glass transition temperature and/or melt temperature to improve the wearability of the tissue pad, which is important when high clamping forces are employed because tissue pads wear faster at higher clamping forces than at lower clamping forces. Applicants found, in one experiment, that a 15% graphite-filled polytetrafluoroethylene tissue pad showed substantially the same wear with a 7 pound clamping force as a 100% polytetrafluoroethylene tissue pad showed with a 1.5 pound clamping force. Having a flexible clamping arm and/or a flexible tissue pad should also improve the wearability of the tissue pad due to the ability of the flexible member to more evenly distribute the load across the entire surface of the tissue pad. Further benefits and expressions of this embodiment are disclosed in U.S. provisional patent application Ser. No. 60/548,301, filed on Feb. 27, 2004 and commonly assigned to the assignee of the present application, and which the entire contents are incorporated by reference herein.

In a fifth expression of the current embodiment, a tissue pad with a base material and at least two filler materials allows the base material and the at-least-two filler materials to be chosen with a different hardness, stiffness, lubricity, dynamic coefficient of friction, heat transfer coefficient, abradability, heat deflection temperature, and/or melt temperature to improve the wearability of the tissue pad, which is important when high clamping forces are employed because tissue pads wear faster at higher clamping forces than at lower clamping forces. Applicants found, in one experiment, that a 15% graphite-filled, 30% PTFE-filled polyimide tissue pad showed substantially the same or better wear with a 4.5 pound clamping force as a 100% polytetrafluoroethylene tissue pad showed with a 1.5 pound clamping force. The advantage of a 15% graphite-filled, 30% PTFE-filled polyimide tissue pad is increased heat resistance, which improves the overall wear resistance of the tissue pad. This polyimide-composite clamp pad has a useful heat resistance up about 800° F. to about 1200° F., as compared to a useful heat resistance up to about 660° F. of a PTFE clamp pad. Alternatively, Other materials are also useful for a portion of the tissue pad (that is element 58b'), such as ceramics, metals, glasses and graphite.

Referring to FIGS. 3a-e, one expression of clamp arm 56 has different shaped slots for accepting two or more tissue pads. This configuration prevents mis-loading of the tissue pads and assures that the appropriate pad is loaded at the correct location within clamp arm 56. For example clamp arm 56 may comprise a distal T-shaped slot 53a for accepting a T-shaped flange 53b' of distal clamp pad 58a' and a proximal wedged-shaped or dove tailed-shaped slot 55a for accepting a wedge-shaped flange 55b' of proximal clamp pad 58b'. Tab stop 51 engages the proximal end of proximal clamp pad 58b' to secure the clamp pads onto clamp arm 56. As would be appreciated by those skilled in the art, flanges 53b' and 55b' and corresponding slots 53a and 55a may have alternate shapes and sizes to secure the clamp pads to the clamp arm. The illustrated flange configurations shown are exemplary only and accommodate the particular clamp pad material of one embodiment, but the particular size and shape of the flange may vary, including, but not limited to, flanges of the same size and shape. For unitary tissue pads, the flange may be of one configuration. Further, other tab stops are possible and may include any of the multiple methods of mechanically attaching the clamp pads to the clamp arm, such as rivets, glue, press fit or any other fastening means well know to the artisan.

Figure 4A:
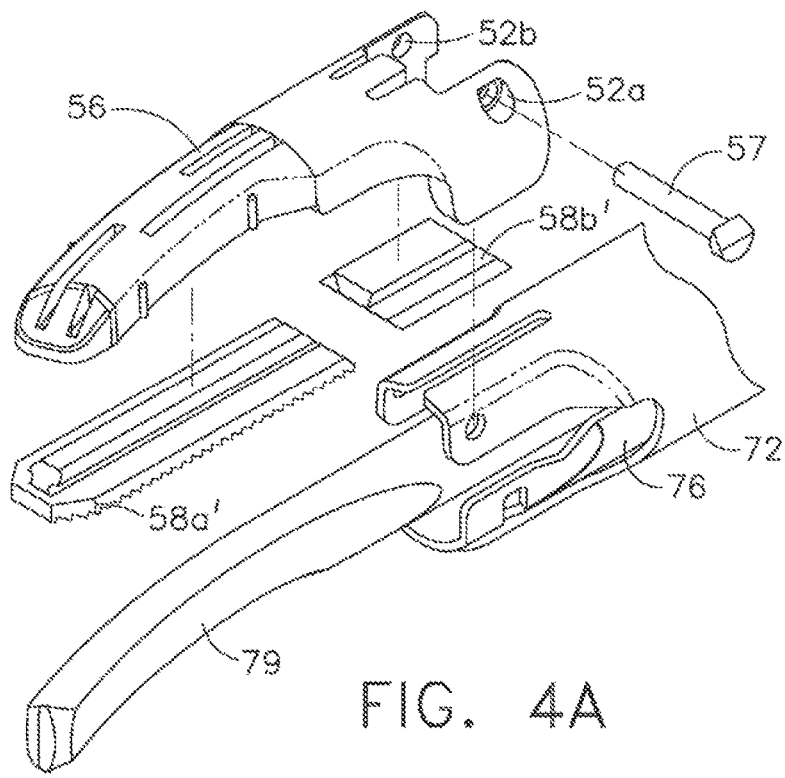
FIG. 4a is a perspective assembly view of the blade, clamp arm, tissue pads and actuator tube with the clamp arm in the closed position.
Figure 4B:
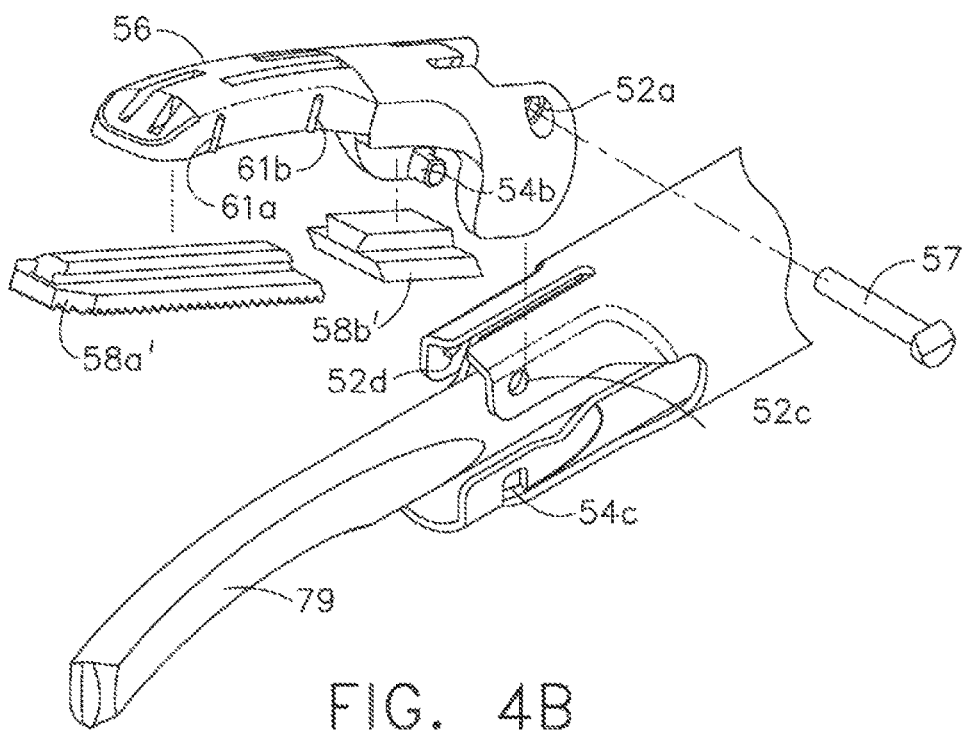
FIG. 4b is a perspective assembly view of the blade, clamp arm, tissue pads and actuator tube with the clamp arm in the open position.

In a second expression of the current embodiment, clamp pads 58a and 58b are cut on a bias so the interface between the two pads creates an overlap to minimize gapping (FIGS. 4a, 4b). For example, a 45 degree biased cut does allow some gapping to occur, but the amount of gap seen by the tissue is minimized.

In a third expression of the current embodiment, clamp arm 56 increases in its height dimension from the distal end to the proximal end (D1<D2). Preferably, D2 is from about 105% to about 120% greater than D1 and more preferably, D2 is from about 108% to about 113% greater than D1, and most preferably, D2 is about 110% greater than D1. Slot 153 accepts the flanges from one clamp pad 58 or two clamp pads 58a and 58b. Tapered clamp arm 56 allows for the use of use flat pads and increases the pressure in the proximal portion of end effector 81 as well as the interference with blade 79. When clamp arm 56 deflects at a greater rate than the blade 79, pressure still exists at the tissue pad and blade interface and no gap is created. Additionally, the increased pressure helps to offset the decreased blade amplitude at the proximal end of blade 79 and provides a relatively constant pressure between the clamp pad 58 and blade 79.

A first expression for a method for inserting clamp pads includes a) inserting first and second clamp pads having a first-shaped flange into a clamp arm 56 having a slot that accepts the first-shaped flange; and b) engaging a pad stop to secure the clamp pads within the clamp arm. In a second expression of this method one clamp pad may be fabricated from a polymeric material such as TEFLON, and the second clamp pad may be fabricated from a base material and at least one filler material, which is a different material from the base material and that clamp arm is fabricated from metal, such as stainless steel, or titanium. The tissue surfaces of the clamp pads may be smooth or have tissue gripping features, such as a saw-tooth configuration.

A third expression for a method for inserting clamp pads includes a) inserting a first clamp pad having a first-shaped flange into a clamp arm having a slot that accepts the first-shaped flange; b) inserting a second clamp pad having a second-shaped flange into the clamp arm having a slot that accepts the second-shaped flange; and c) engaging a pad stop to secure the clamp pads within the clamp arm. In a fourth expression of this method one clamp pad may be fabricated from a polymeric material such as TEFLON, and the second clamp pad may be fabricated from a base material and at least one filler material, which is a different material from the base material and that clamp arm is fabricated from metal, such as stainless steel, or titanium. The tissue surfaces of the clamp pads may be smooth or have tissue-gripping features, such as a saw-tooth configuration.

A first expression of a method for replacing clamp pads 58 would include the steps of: a) disengaging a pad stop; b) removing a first clamp pad from the clamp arm; c) removing a second clamp pad from the clamp arm; d) inserting third and fourth clamp pads into the clamp arm; and e) engaging a pad stop to secure the third and fourth clamp pads within the clamp arm. In a second expression of this method one of the third and fourth clamp pads may be fabricated from a polymeric material such as TEFLON, and the other clamp pad may be fabricated from a base material and at least one filler material, which is a different material from the base material and that clamp arm is fabricated from metal, such as stainless steel, or titanium. The tissue surfaces of the clamp pads may be smooth or have tissue gripping features, such as a saw-tooth configuration.

Referring now to FIG. 4, pivotal movement of the clamp member 60 with respect to blade 79 is affected by the provision of a pair of pivot points on the clamp arm 56 that interface with the outer tube 72 and inner tube 76 respectively. The outer tube 72 is grounded to handle 68 through rotation knob 29. Clamp arm 56 is pivotally connected to outer tube 72 via corresponding through holes 52a and 52b on clamp arm 56 and 52c and 52d on outer tube 72. A securing pin or rivet 57 slides through holes 52a-d to secure clamp arm 56 to outer tube 72. In one embodiment pin 57 is laser welded to clamp arm 56 so that pin 57 is fixed to clamp arm 56 and rotates relative to outer sheath 72.

Inner tube 76 translates along the longitudinal axis of outer tube 72 and is grounded to the handle 68 through rotation knob 29. Pivot studs 54a,b (54a not shown) on clamp arm 56 engage pivot holes 54c,d (54d not shown) at the distal end of inner tube 76. The pivotal connection of clamp arm 56 to the inner and outer tubes 76, 72 provide more robustness to the end effector 81 and minimize failure modes due to excessive axial or torsional abuse loads. Further, the embodiment increases the effectiveness of the end effector 81 to provide clamp forces in excess of 1.5 lbs. Reciprocal movement of the actuating member 76, relative to the outer sheath 72 and the waveguide 80, thereby affects pivotal movement of the clamp arm 56 relative to the end-blade 79.

Figure 4C:
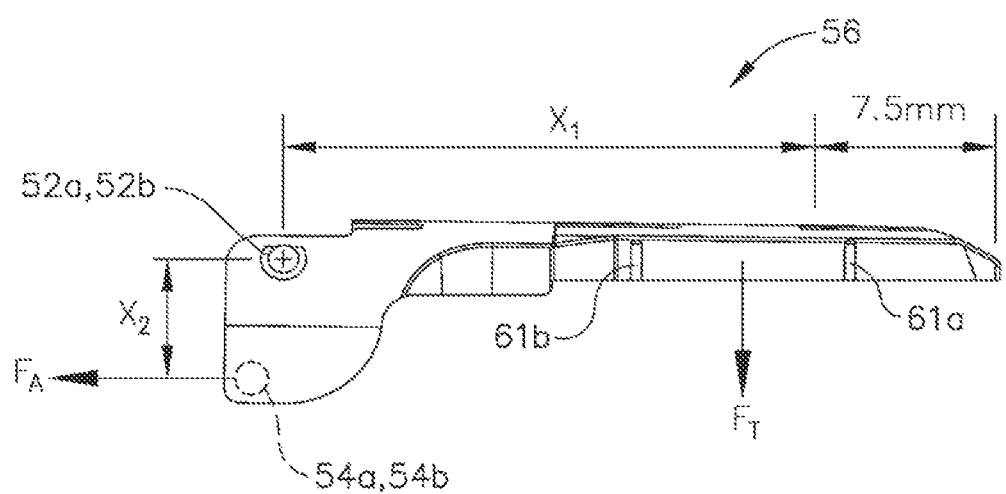
FIG. 4c is a schematic of a clamp arm in accordance with the present invention illustrating force calculations.
Figure 16A:
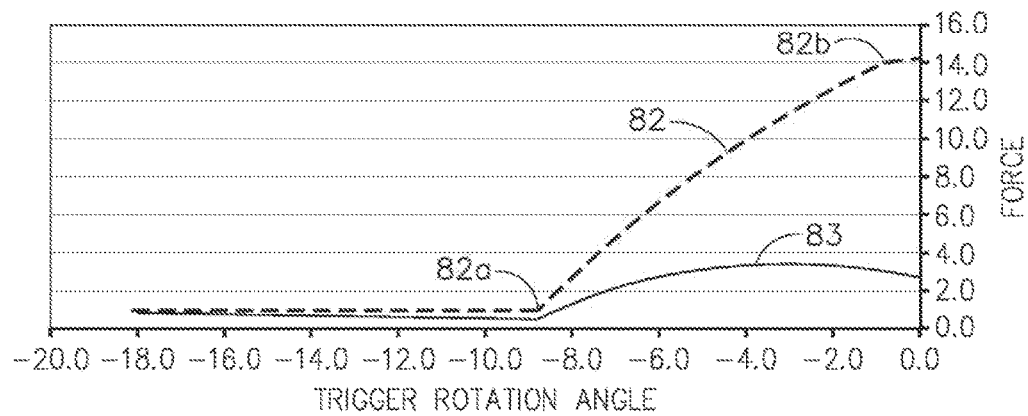
FIG. 16a-c are force curves illustrating various forces as a function of the trigger position and tissue conditions.
Figure 16B:
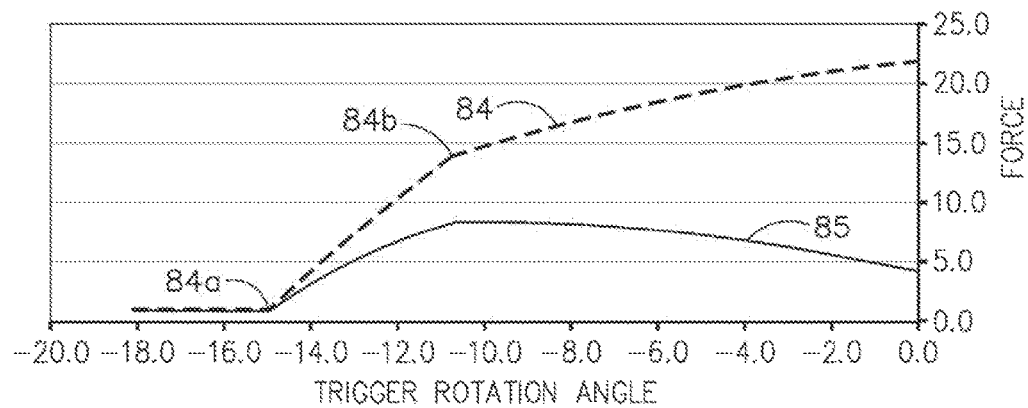
Figure 16C:
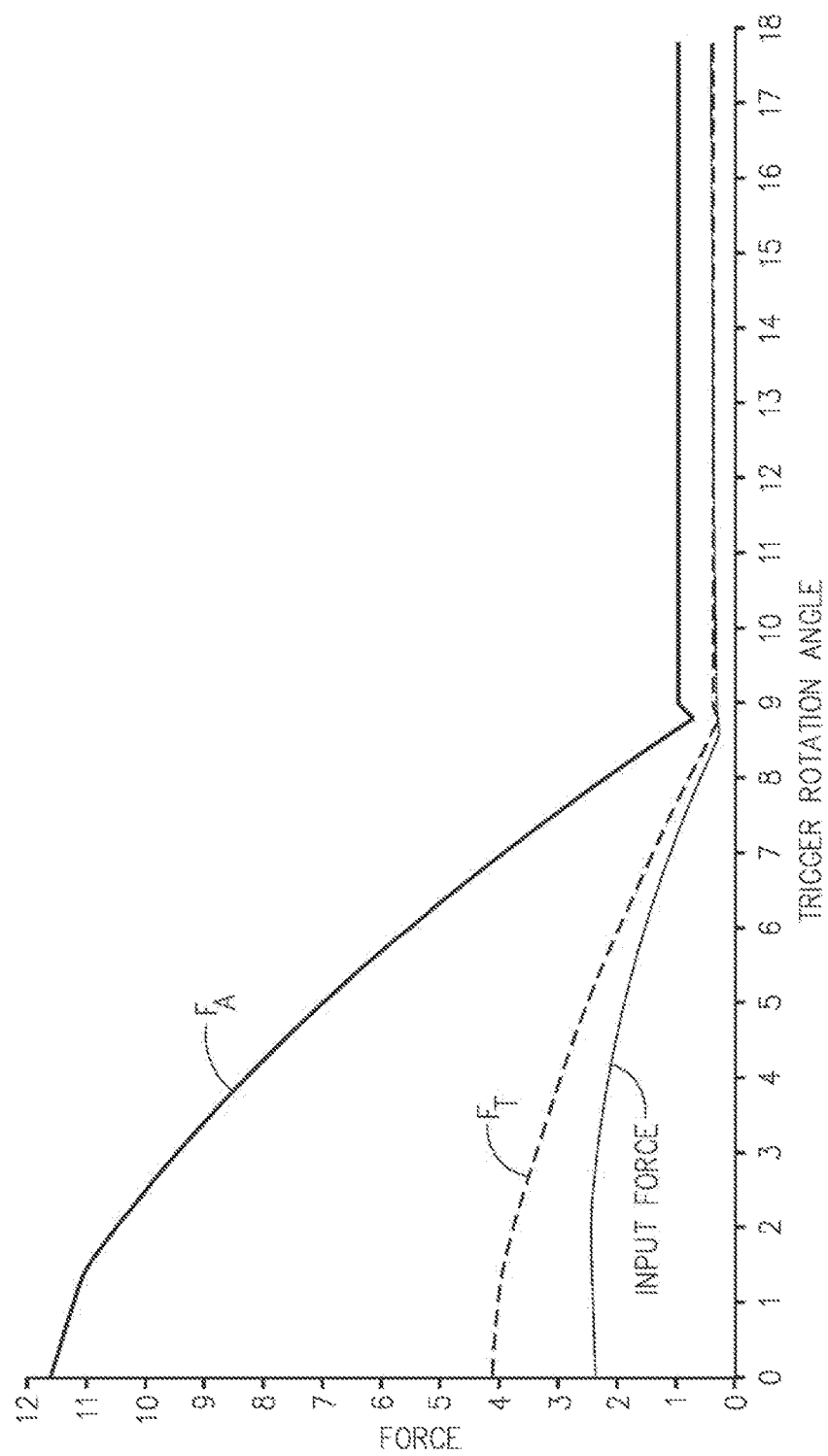

FIG. 4c illustrates a force diagram and the relationship between the actuation force FA (provided by actuation member 76) and transection force FT (measured at the midpoint of the optimal tissue treatment area).

$$FT=FA(X2/X1) \qquad \text{Equation [1]}$$

Where FA equals the spring preload of proximal spring 94 (less frictional losses), which, in one embodiment, is about 12.5 pounds, and FT equals about 4.5 pounds as shown in FIG. 16c. FIG. 16c provides a graphical illustration of FT and FA as a function of trigger 34 movement as well as input forces at trigger 34.

FT is measured in the region of the clamp arm/blade interface where optimal tissue treatment occurs as defined by tissue marks 61a and 61b. Tissue marks 61a, b are etched or raised on clamp arm 56 to provide a visible mark to the surgeon so the surgeon has a clear indication of the optimal tissue treatment area. Tissue marks 61a, b are about 7 mm apart in distance, and more preferably 5 mm apart in distance.

Rotation of the transmission assembly 71 of ultrasonic surgical instrument 100 may be affected together with relative rotational movement of ultrasonic transducer 50 with respect to instrument handle assembly 68. In order to join the transmission assembly 71 to the ultrasonic transducer 50 in ultrasonic-transmitting relationship, the proximal portion of the outer sheath 72 may be provided with a pair of wrench flats 46. The wrench flats 46 allow torque to be applied by a suitable torque wrench or the like to thereby permit the waveguide 80 to be joined to the ultrasonic transducer 50. The ultrasonic transducer 50, as well as the transmission assembly 71, is thus rotatable, as a unit, by suitable manipulation of rotation knob 29, relative to handle assembly 68 of the instrument. The interior of handle assembly 68 is dimensioned to accommodate such relative rotation of the ultrasonic transducer 50. A spring 28 is loaded against rotation knob 29 and an inner housing surface 65. Spring 28 provides a compression or force against rotation knob 29 to inhibit inadvertent rotation of end effector 81.

Referring now to FIGS. 2, 5, 6 and 16, force limiting mechanism 91 provides a first and second compression spring, distal spring 96 and proximal spring 94. Distal spring 96 is operationally coupled to yoke 33, which in turn is driven by trigger 34. Proximal spring 94 is in operational relationship with distal spring 96. Distal spring 96 generates the end effector load and proximal spring 94 maintains the consistency of the end effector load. As a result, the end effector load is more tightly controlled and component abuse load conditions are reduced. Washers 97 and 95 are a safe guard against distal spring 96 being fully compressed (FIG. 5), thereby preventing the spring material to yield and render spring 96 useless in subsequent clamp arm closures. As would be appreciated by one skilled in the art, the application of a dual spring force limiting system has applicability in other energy-based surgical devices (such as RF, microwave and laser) that encounter clamping forces, as well as mechanical devices, such as, clip appliers, graspers and staplers.

In one expression of the current embodiment, distal spring 96 has a spring constant greater than 100 pounds per inch and preferably greater than 125 pounds per inch and most preferably about 135 pounds per inch. It is not required that distal spring 96 be preloaded, but may be preloaded at less than 10 pounds, and preferably less than 5 pounds, and most preferably at about 1 pound. Proximal spring 94 has a spring constant greater than 25 pounds per inch and preferably greater than 50 pounds per inch and most preferably about 70 pounds per inch. Proximal spring 94 is preloaded to a force necessary to achieve the desired transection force as noted in Equation 1, above, and is a function of the mechanical advantage of the clamp arm 56 coupling means and frictional losses in the device. In a second expression of the current embodiment, proximal spring 94 is preloaded at about 12.5 pounds.

Referring now to FIG. 16a, curve 82 illustrates actuation member 76 force and curve 83 represents trigger 34 force as a function of the angular rotation of trigger 34 (on the x-axis, −18.0 is the clamp arm 56 fully open and 0.0 is the clamp arm fully closed and against blade 79) under no tissue or minimal tissue load operation. Point 82a represents the point at which yoke 33 begins to deflect or compress distal spring 96 and the actuation member 76 force increases as trigger 34 is depressed further until the force reaches the preload value of proximal spring 94 at inflection point 82b, and the slope of the force curve decreases.

In FIG. 16b, curve 84 illustrates actuation member 76 force and curve 85 represents trigger 34 force as a function of the angular rotation of trigger 34 under abusive tissue load operation, whereby tissue completely fills the end effector in the open position. Point 84a represents the point at which yoke 33 begins to deflect or compress distal spring 96 and the actuation member 76 force increases as trigger 34 is depressed until the force reaches the preload value of proximal spring 94 at inflection point 84b, at which point the slope of the force curve decreases.

Figure 5:
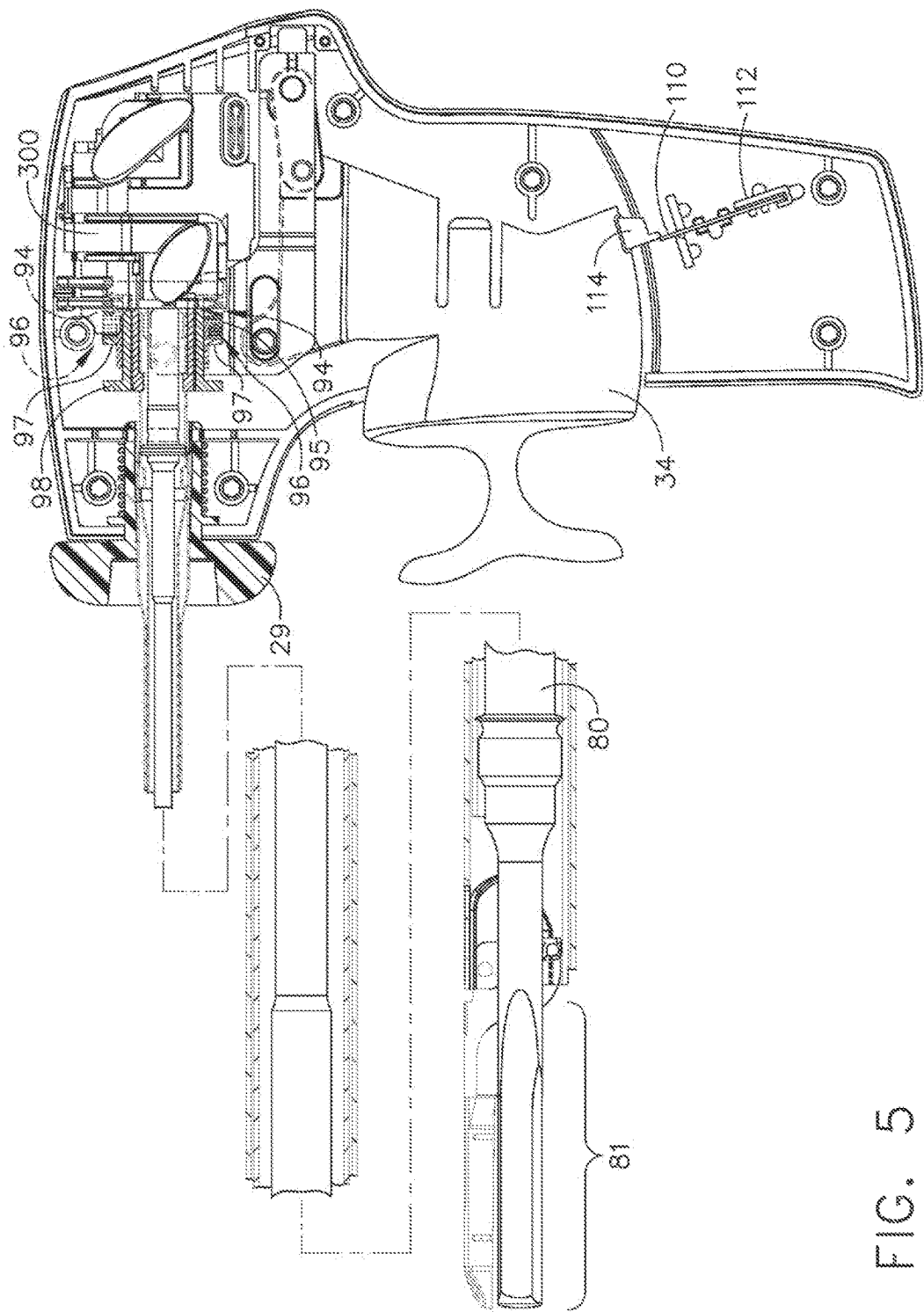
FIG. 5 is a cutaway elevation view of the housing portion of an ultrasonic surgical instrument in accordance with an embodiment of the present invention illustrating force-limiting springs and clamp closure detent mechanism and partial cutaway elevation view of the transmission rod and end effector.
Figure 6A:
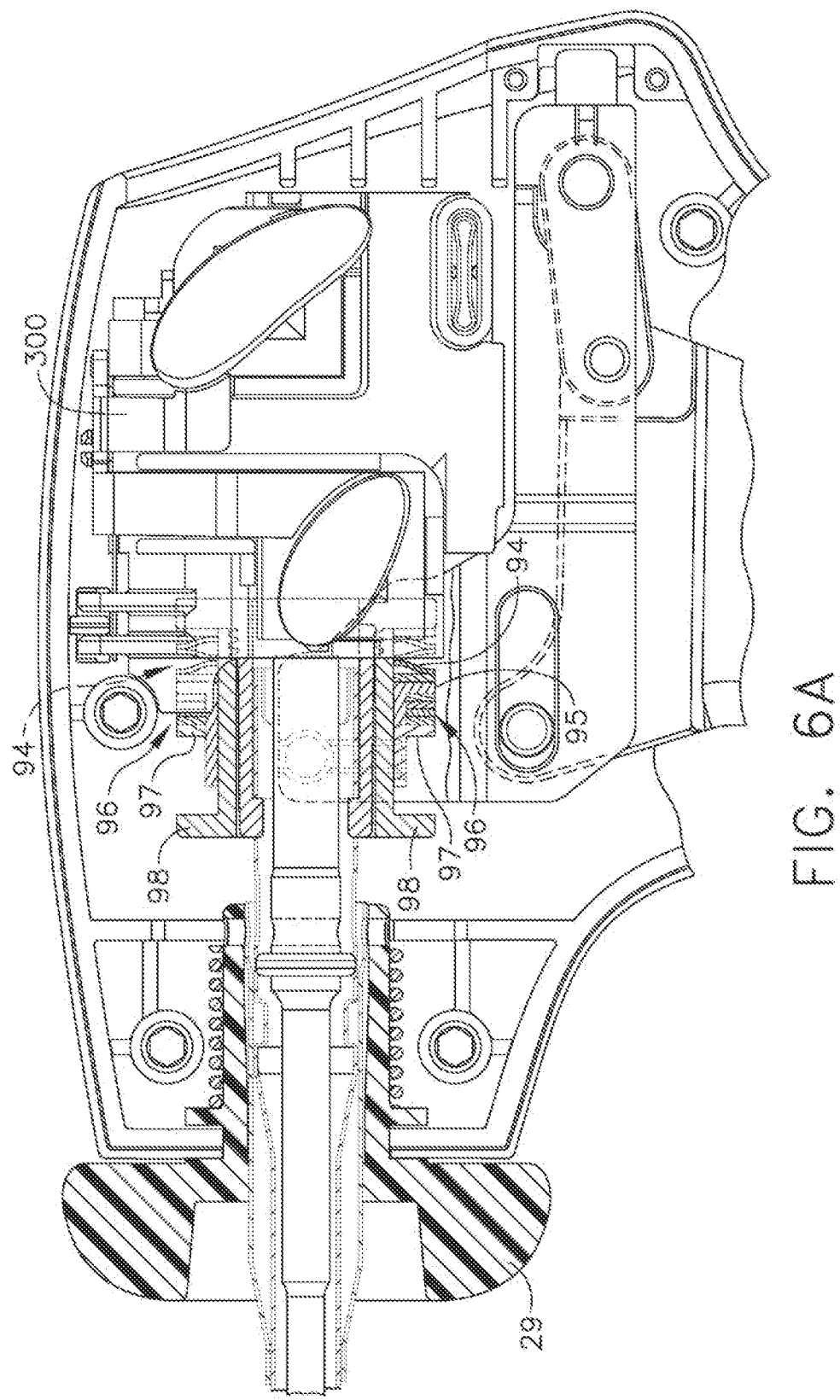
FIG. 6a is an exploded view of the housing illustrating the thumb actuation buttons and switch assembly and linkage of the finger grip clamp actuator.
Figure 6B:
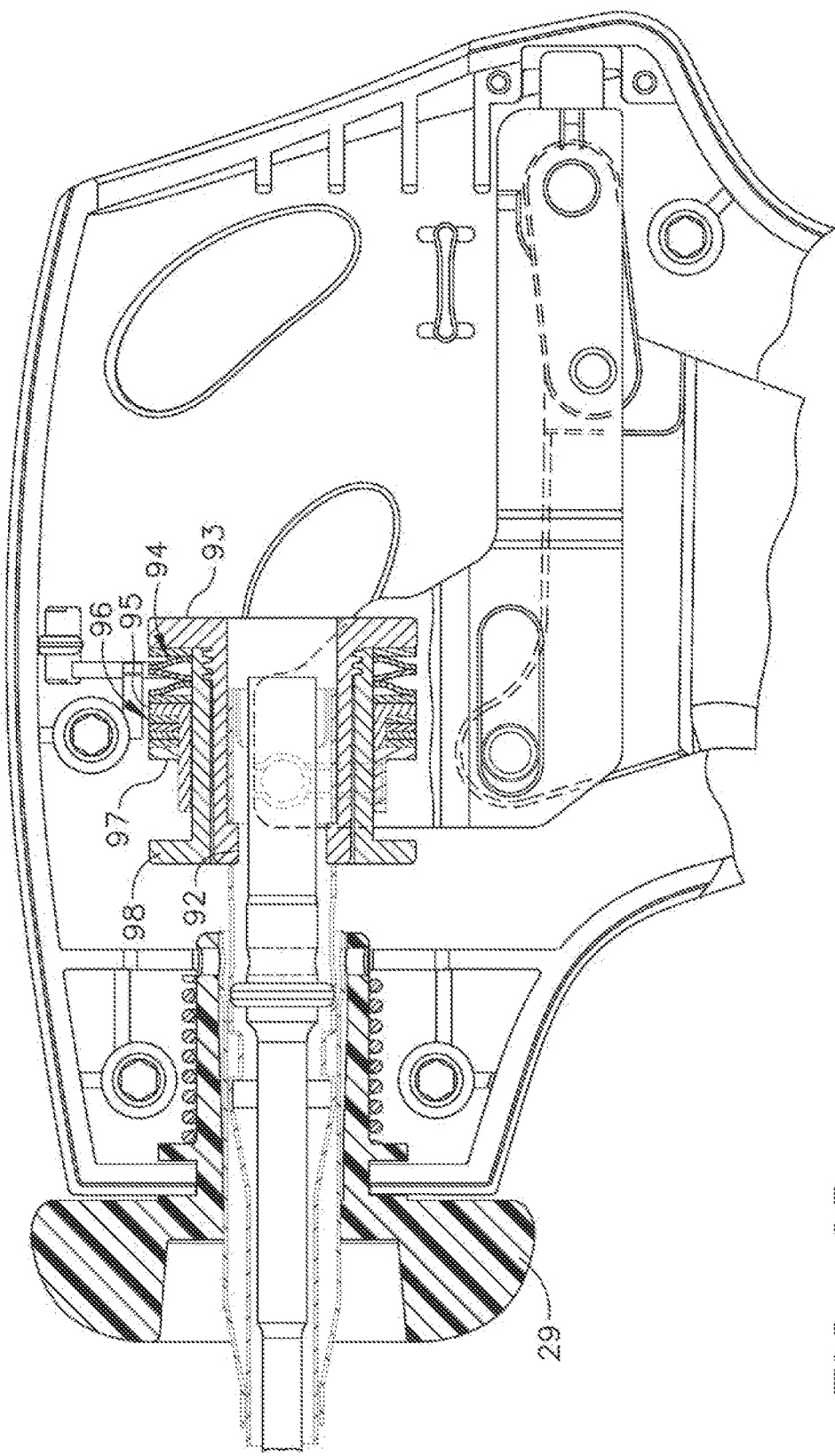
FIG. 6b is an exploded view of the housing with the switch assembly removed for clarity.
Figure 7:
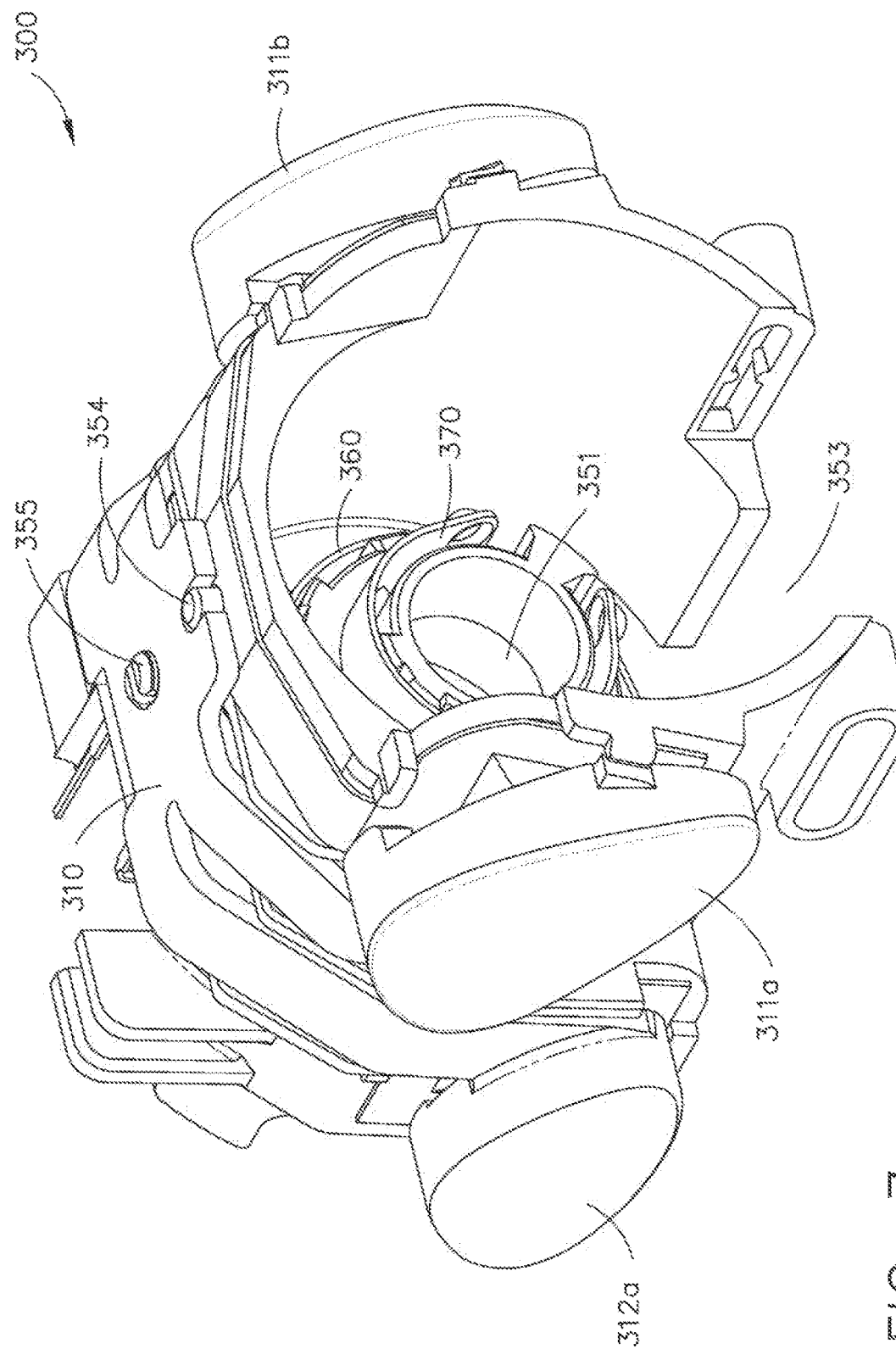
FIG. 7 is a perspective assembly view of the switch assembly and electrical ring contactors.

Referring now to FIGS. 2 and 5, surgical instrument 100 further provides for a means for indicating to the surgeon that the trigger has reached full travel and the clamp arm 56 is applying the correct coaptation force to the tissue. This is useful during protracted surgical operations or tissue transection activities when the surgeon's grip may relax, just a bit, without the surgeon's knowledge, and the pressure delivered to the tissue from the clamp arm 56 may be unknowingly decreased.

In one expression of the current embodiment, a detent spring 110 is supported within a detent support 112 located within housing portion 69. A detent tab 114 on trigger 34 engages and snaps back detent spring 110 when trigger 34 is fully closed or actuation member 76 has reached it most proximal travel. Detent spring 110 is generally planar and made of a flexible plastic that adequately deflects when it engages tab 114 thereby providing an audible and/or tactile signal to the surgeon that there is full end effector 81 closure. Advantageously, tab 114 strikes and deflects detent spring 110 when trigger 34 is rotated from the full closure position and in the opposite direction thereby providing an audible and/or tactile signal to the surgeon that full closure of end effector 81 no longer exists. As would be appreciated by the skilled artisan, the indicating means may be either tactile, audible or visual or a combination. Various types of indicators may be used including dome switches, solid stops, cantilever springs or any number of mechanical or electrical switches known to those skilled in the art. Further various means may be used to provide feedback to the surgeon, including, but not limited to, lights, buzzers, and vibratory elements.

Referring now to FIGS. 1, 2 and 6-8 housing 68 includes a proximal end, a distal end, and a cavity 59 extending longitudinally therein. Cavity 59 is configured to accept a switch assembly 300 and the transducer assembly 50, which interfaces with housing 68 via switch assembly 300.

Transducer 50 includes a first conductive ring 400 and a second conductive ring 410 which are securely disposed within the transducer body 50. In one expression of the current embodiment, first conductive ring 400 comprises a ring member, which is disposed between the transducer 50 and the horn 130. Preferably the first conductive ring 400 is formed adjacent to or as part of the flange member 160 within the cavity 162 and is electrically isolated from other electrical components. The first conductive ring 400 is anchored to and extends upwardly from a non-conductive platform or the like (not shown) which is formed within the transducer body 50. The first conductive ring 400 is electrically connected to the cable 22 (FIG. 1) by means of one or more electrical wires (not shown), which extend along the length of the transducer body 50 to the first conductive ring 400.

The second conductive ring 410 of the transducer 50 similarly comprises a ring member that is disposed between the transducer body 150 and the horn 130. The second conductive ring 410 is disposed between the first conductive ring 400 and the horn 130 and therefore the first and second conductive rings 400, 410 are concentric members. The second conductive ring 410 is likewise electrically isolated from the first conductive ring 400 and other electrical components contained within the transducer 50. Similar to the first conductive ring 400, the second conductive ring 410 preferably is anchored to and extends upwardly from the non-conductive platform. It will be understood that the first and second conductive rings 400, 410 are sufficiently spaced from one another so that they are electrically isolated from each other. This may be accomplished by using one or more spacers 413 disposed between the first and second conductive rings 400, 410 or between the rings 400, 410 and other members within the transducer 50. The second conductive ring 410 is also electrically connected to the cable 22 (FIG. 1) by means of one more electrical wires (not shown), which extend along the length of the transducer 50 to the second conductive ring 410. The second conductive ring 410 is thus provided to partially define a second electrical pathway from the cable 22 to the switch mechanism 300. A suitable ultrasonic transducer 50 is Model No. HP054, sold by Ethicon Endo-Surgery, Inc. of Cincinnati, Ohio.

In one expression of the current embodiment, the distal end of transducer 50 threadedly attaches to the proximal end of transmission rod 80. The distal end of transducer 50 also interfaces with switch assembly 300 to provide the surgeon with finger-activated controls on surgical instrument 100.

Switch assembly 300 comprises a pushbutton assembly 310, a flex circuit assembly 330, a switch housing 350, a first spring slip ring conductor 360 and a second spring slip ring conductor 370. Switch housing 350 is generally cylindrical and is supported within handle assembly 68 by way of corresponding supporting mounts on switch assembly 350 and housing portions 69 and 70. Housing 350 defines a first cavity 353, a mounting boss 352 and a second cavity 351. Cavity 353 is sized to accept the proximal end of transducer 50, whereby horn 130 passes through cavity 351 to interface with transmission rod 80. Mounting boss 352 accepts slip ring conductors 360 and 370, which in turn electrically engage ring contacts 400 and 410, respectively. An alignment pin 354 and snap-fit pin 355 align with corresponding apertures of the flex circuit assembly 330 and pushbutton assembly 310 to secure all components together as discussed below.

Figure 8A:
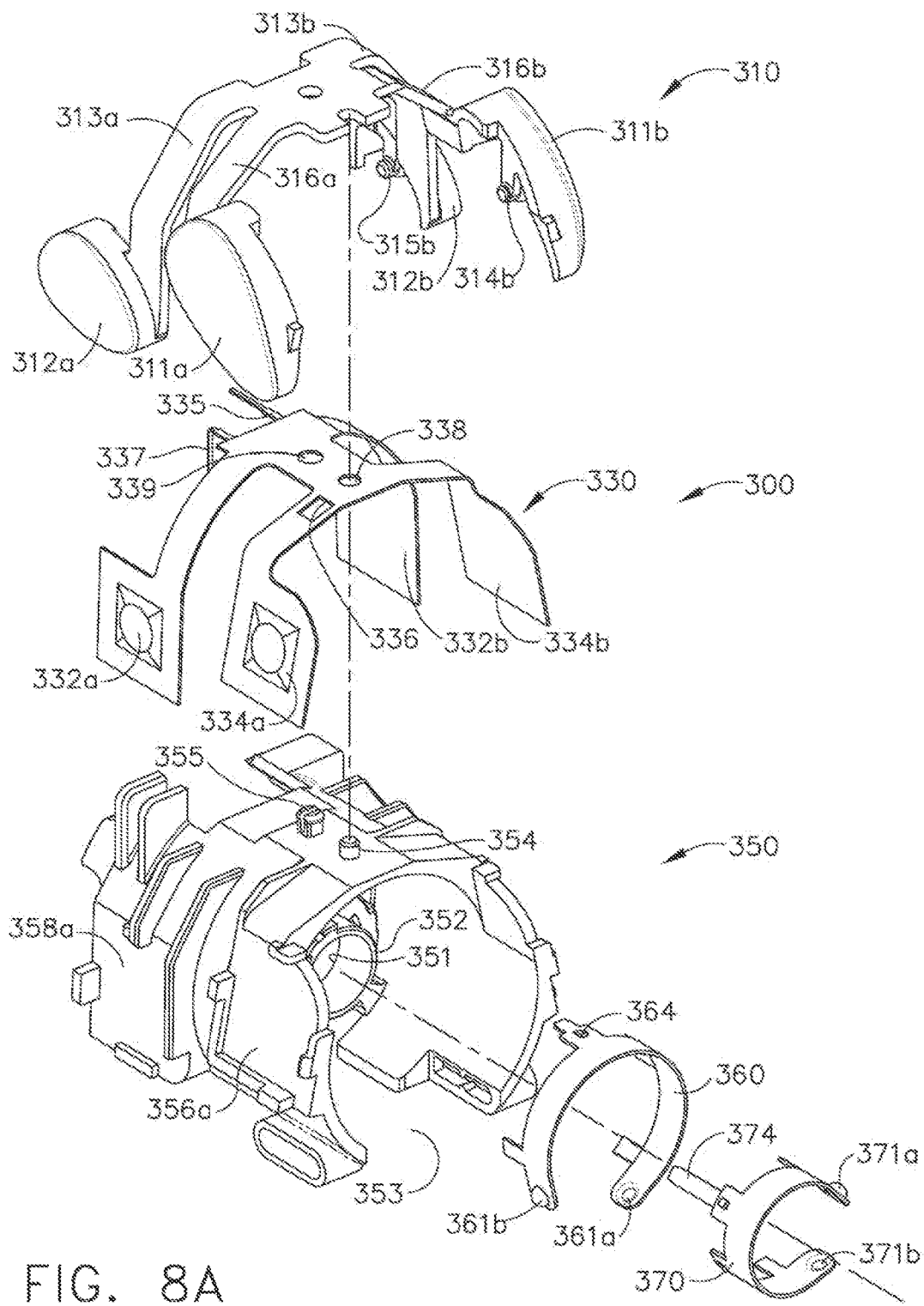
FIG. 8a is a perspective assembly view of the switch assembly and electrical ring contactors.
Figure 8B:
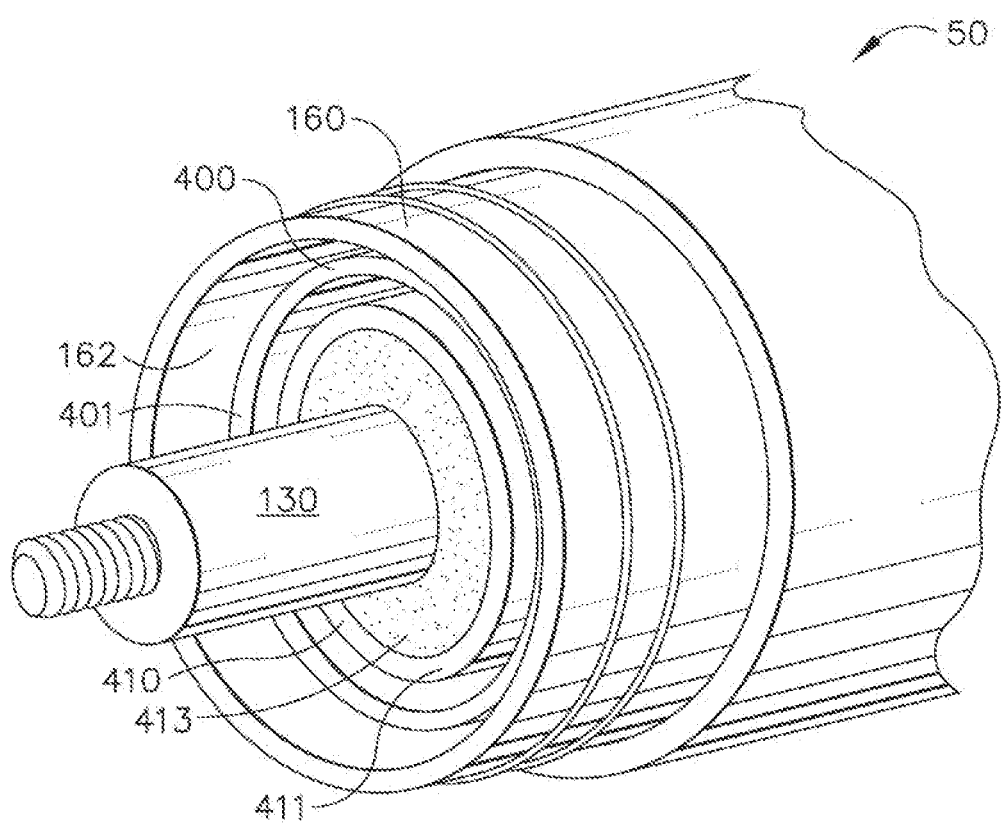
FIG. 8b is a perspective view of the proximal end of the transducer illustrating conductor rings.
Figure 8C:
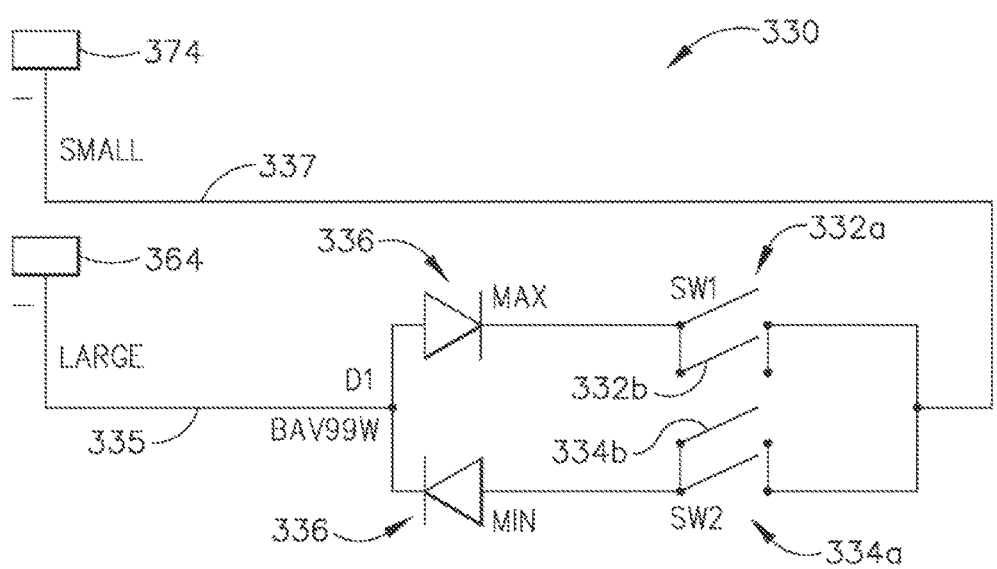
FIG. 8c is an electrical schematic of the pushbutton circuit.
Figure 9:
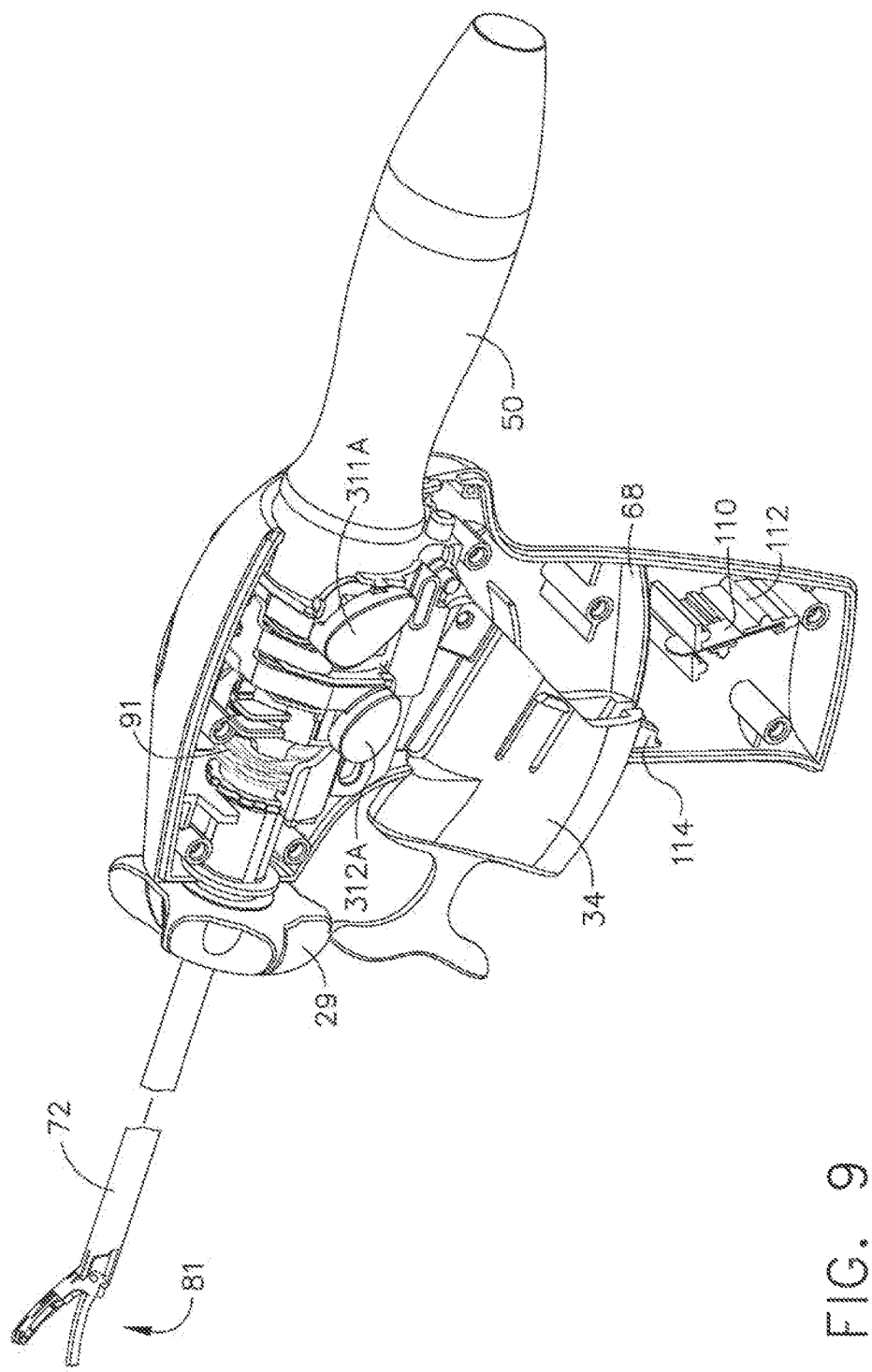
FIG. 9 is a perspective view of an ultrasonic surgical instrument with a cut away view of the housing and connected to a transducer.

With particular reference now to FIG. 8a, slip ring conductors 360 and 370 are generally open-ended O-shaped springs that slip onto mounting boss 352. Each spring slip-ring comprises two pressure point contacts (361a-b and 371a-b) that contact the respective ring conductor 400 and 410 of transducer 50. The spring tension of the slip rings 360 and 370 cause positive contact between contacts 361a-b, 371a-b and conductors 400 and 410. It is evident that the slip-ring construction allows electrical contact to be made even as transducer 50 may be rotated by the surgeon during use of the instrument. Posts 364 and 374 of the respective slip rings electrically connect to the respective conductor within flex circuit 330 to complete the electrical circuit as shown in FIG. 8c.

A flex circuit 330 provides for the electro-mechanical interface between pushbuttons 311a, b, 312a, b and the generator 30 via transducer 50. Flex circuit comprises four dome switches 332a,b and 334a, b that are mechanically actuated by depressing pushbuttons 311a, b or 312a, b, respectively of corresponding pushbutton assembly 310. Dome switches 332 and 334 are electrical contact switches, that when depressed provide an electrical signal to generator 30 as shown by the electrical wiring schematic of FIG. 8c. Flex circuit 330 also comprises two diodes within a diode package 336, also illustrated in FIG. 8c. Flex circuit 330 provides conductors, 335 and 337 as is known to those in the art, that connect to slip ring conductors 360 and 370 via electrical tabs 364 and 374, respectively, which in turn provide electrical contact to ring conductors 400 and 410, which in turn are connected to conductors in cable 22 that connect to generator 30. Tabs 364 and 374 are soldered to conductors 335 and 337.

Flex circuit 330 generally wraps around switch housing 350 so that dome switches 334a, b and 332a, b interface with the corresponding backing surfaces 356a, b and 358a, b on switch housing 350. Backing surfaces provide a firm support for the dome switches during operation, discussed below. Dome switches 334a, b and 332a, b may be fixedly attached to backing surfaces 356a, b and 358a, b by any convenient method, such as, an adhesive. Flex circuit is secured to switch housing 350 via alignment pin 354 and snap-fit pin 355 on switch assembly 350 and corresponding alignment hole 338 and snap-fit hole 339 on flex circuit 330.

Layered on top of flex circuit is pushbutton assembly 310, which has a corresponding saddle-shape as flex circuit 330, and generally wraps around switch housing 350. Pushbutton assembly 310 comprises four pushbuttons, distal pushbuttons 312a, b and proximal pushbuttons 311a, b which have corresponding pressure studs 315a, b and 314a, b. The pushbuttons are connected to cantilever elements 313a, b and 316a, b, which provide a spring-back action after the pushbuttons are depressed. As is readily apparent, by depressing pushbuttons 311 and 312 the corresponding pressure studs 314 and 315 depress against corresponding dome switches 334 and 332 to activate the circuit illustrated in FIG. 8c. Switches 312a and b are in parallel so that a surgeon may operate the pushbuttons using either a left hand or a right hand. Likewise, switches 311a and b are in parallel so that a surgeon may operate the pushbuttons using either a left hand or a right hand. When the surgeon depresses either switch 312a or 312b, the generator will respond with a certain energy level, such as a maximum ("max") power setting; when the surgeon depresses either switch 311a or 311b, the generator will respond with a certain energy level, such as a minimum ("min") power setting, which conforms to accepted industry practice for pushbutton location and the corresponding power setting.

Alternatively, the pushbuttons may be molded into the switch housing 350 or into the handle assembly 68 to reduce the number of components and increase the reliability of the overall device. The pushbuttons may be attached through small cantilever sections, which allow for sturdy attachment of the pushbutton to the other components, while at the same time allowing for a low force to activate the pushbuttons.

Referring now to FIGS. 12-15, one expression of the current embodiment allows switches 311a, b and 312a, b configured in such a way to provide an ergonomically pleasing grip and operation for the surgeon. Switches may be placed in the range of the natural swing of the surgeon's thumb, whether gripping surgical instrument 100 right-handed or left handed. In a second expression of the current embodiment, the switches are placed on housing 68 to prevent inadvertent button activation on the side of the instrument opposite the thumb while the surgeon depresses trigger 34 or rotates rotation knob 29. In a third expression of the current embodiment a series of partitions, such as ridges and/or depressions or "peaks and valleys" that are integrated onto the housing 68. In one example the housing defines a first surface and the series of partitions define at least one second surface such that the second surface is higher than the housing surface. The partition may also define a third surface that is lower than the housing surface. As can be seen in FIGS. 1, 2 switches 312a, b are surrounded by an upper ridge 320 and a lower ridge 324. Ridges 320 and 324 may be discrete physical features, both separated from each other, or ridges 320 and 324 may be continuous in nature without departing from the scope of the invention. Further, the ridges 320 and 324 may continue across the entire upper portion of housing 68, as shown in FIGS. 12-15, or ridges 320 and 324 may be more discrete as shown in FIGS. 1 and 2. This construction and situation of switches 312a, b prevent the risk of inadvertent button activation even if a finger crosses over the button due to the fact that the ridges cause the finger to pass above the plane of the button. The ridges also provide tactile feedback to the surgeon as to the location of the pushbuttons and whether the button represents min or max power activation. As is readily evident, switches 312*a, b* are surrounded by ridges 320 and 324 and pushbuttons 311*a,b* are situated above and proximal of ridge 320. Such tactile feedback is essential to the surgeon, so the surgeon may continuously assess the surgical site, but confidently understand which pushbuttons are being activated. In a further expression of the current embodiment, switch 312*a, b* are nestled within a depression 322 and further surrounded by ridges 320 and 324.

Figure 12:
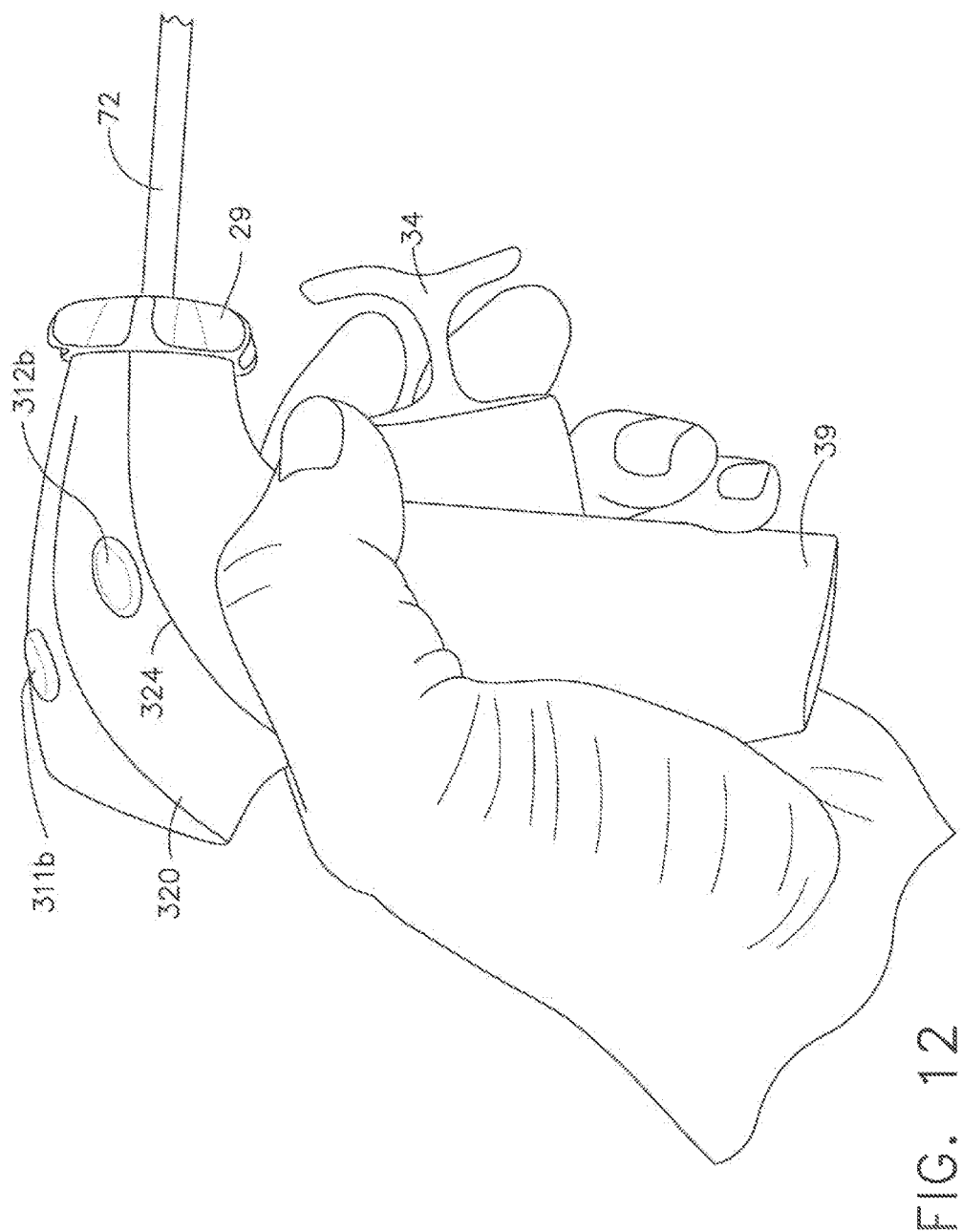
FIG. 12 is an elevation view of a left-handed grip of an embodiment of an ultrasonic surgical instrument in accordance with the present invention.

Referring to FIG. 12, a surgeon's left hand is accessing instrument 100. The fore finger and middle finger are poised to activate trigger 34, and the ring finger and pinkie grasp hand grip 39. The thumb is conveniently positioned to sweep upward to activate pushbutton 312*a* or 311*a*. Ridges 320 and 324 extend across the upper portion of housing 69.

Figure 13:
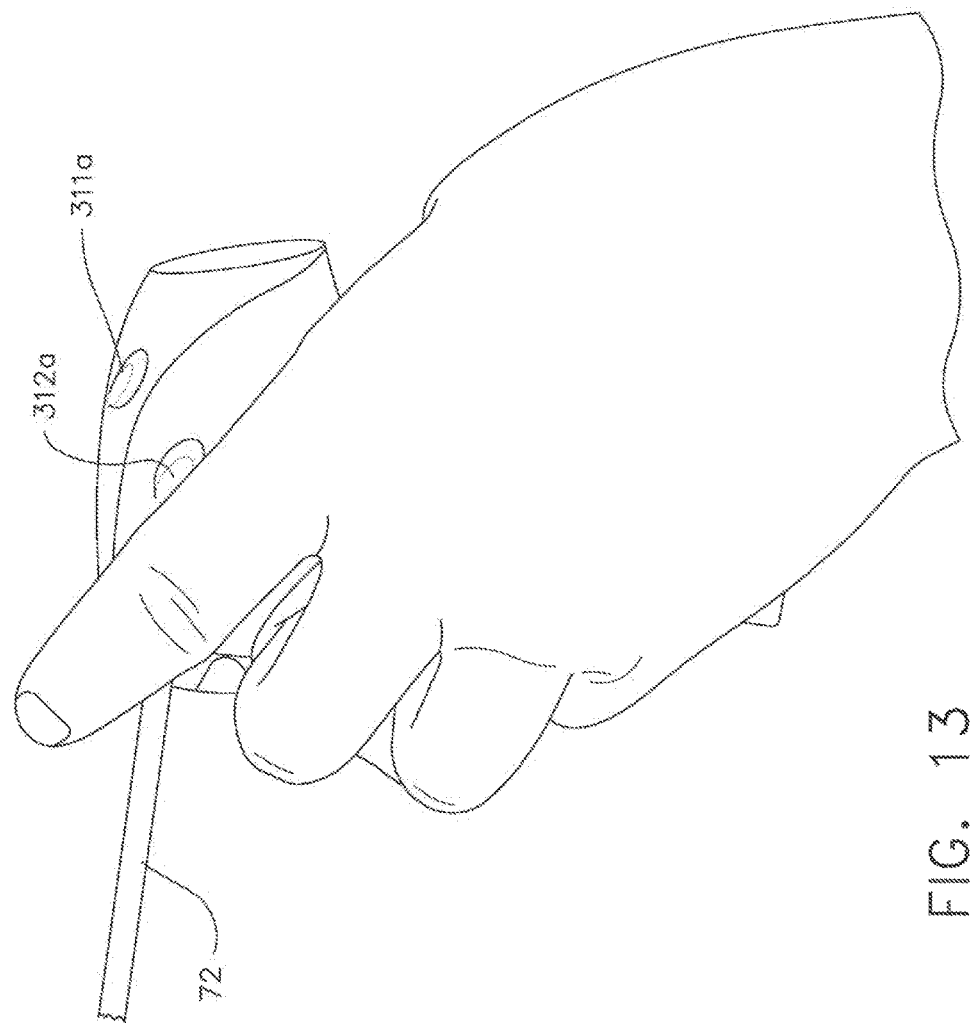
FIG. 13 is an elevation view of a left-handed grip of an ultrasonic surgical instrument in accordance with an embodiment of the present invention with the index finger accessing the rotation wheel.

In FIG. 13, the opposite side of instrument 100 shown in FIG. 12 is illustrated showing pushbuttons 311*b* and 312*b*. Here the surgeon's forefinger is accessing rotation knob 29 to rotate end effector 81. As can be seen, pushbutton 312*b* is subject to inadvertent activation by the forefinger. However, ridge 324 causes the forefinger to elevate above the plane of pushbutton 312*b* thereby reducing the risk of inadvertent activation.

Figure 14:
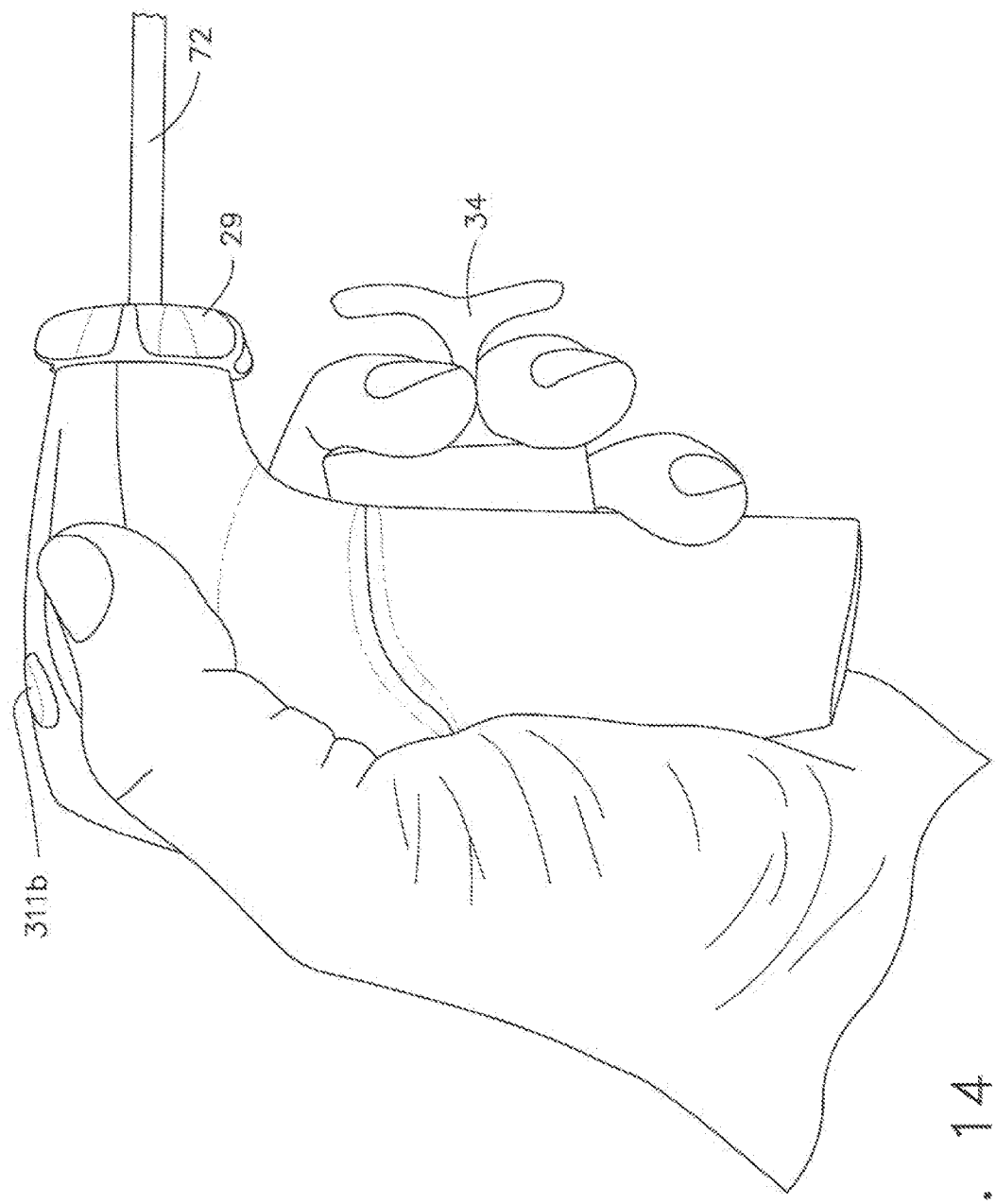
FIG. 14 is an elevation view of a left-handed grip of an ultrasonic surgical instrument in accordance with the present invention with the thumb accessing a first activation button.

In FIG. 14, the surgeon has depressed trigger 34 to close clamp arm 56 against blade 79, and the left thumb has easily accessed pushbutton 312*b* to activate max power.

Figure 15:
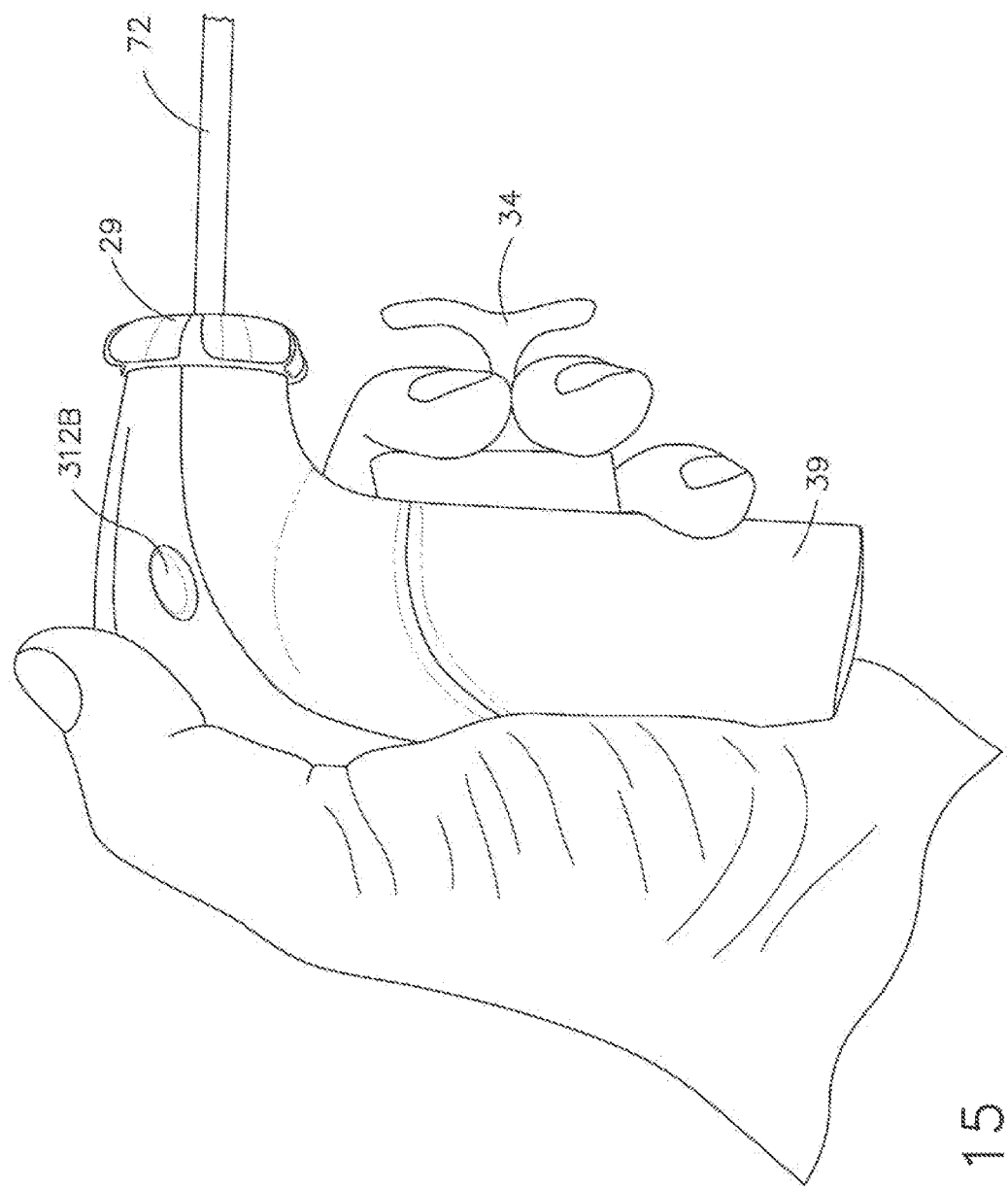
FIG. 15 is an elevation view of a left-handed grip of an ultrasonic surgical instrument in accordance with the present invention with the thumb accessing a second activation button.

In FIG. 15, the surgeon has depressed trigger 34 to close clamp arm 56 against blade 79, and the left thumb has easily accessed pushbutton 311*b* to activate min power.

Figure 17:
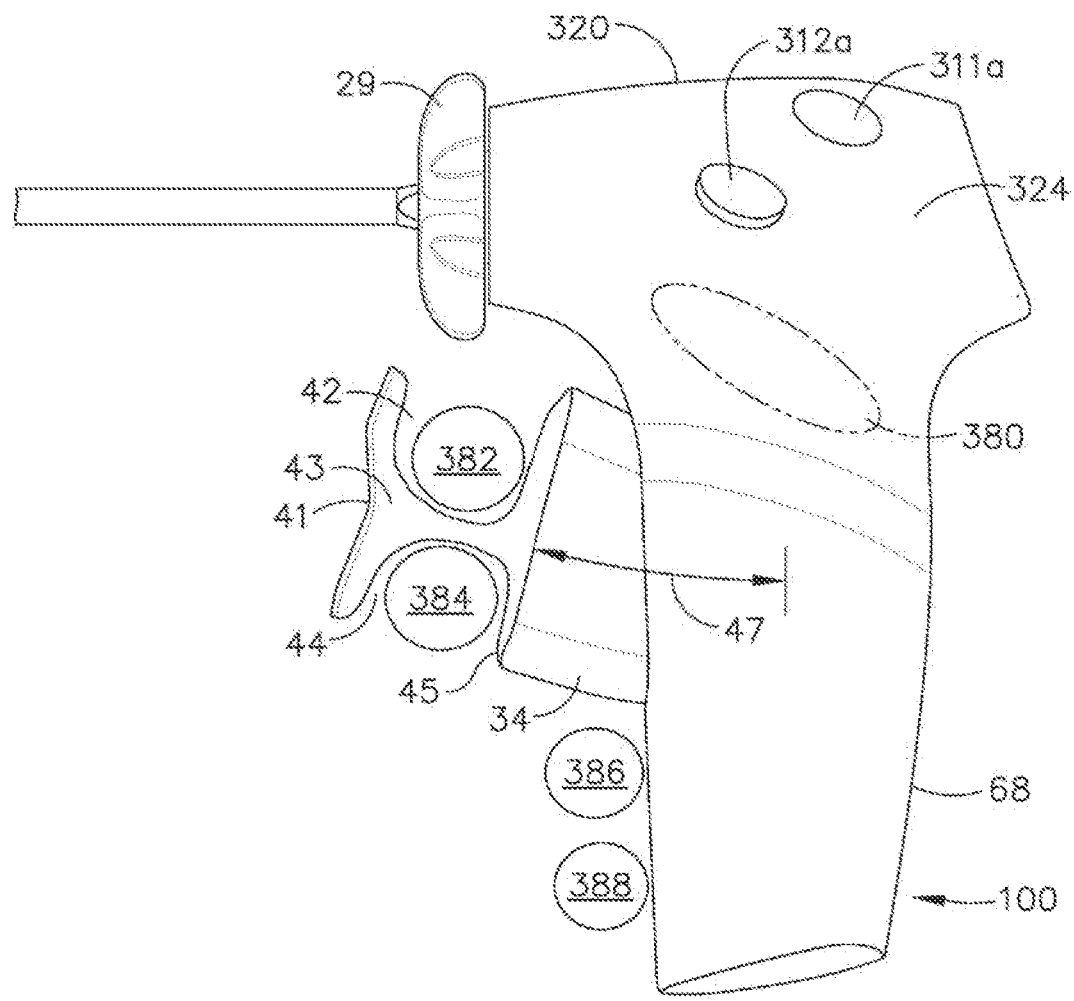
FIG. 17 is an elevation view of the surgical instrument with graphical illustrations of the surgeon finger placement.

Referring to FIG. 17, an expression of surgical instrument 100 is shown graphically illustrating a surgeon's finger placement on instrument 100. Instrumental in the activation of the instrument 100 is the placement of the forefinger 382 and middle finger 384 on trigger 34. (Using the forefinger and middle finger to activate trigger 34 is exemplary only. Surgeons with smaller hands may opt to activate trigger 34 with the middle finger and ring finger, thereby making the forefinger available to rotate knob 29 or even use the ring finger and pinkie to active trigger 34.) Trigger 34 comprises a base element 45, which comprises the detent tab 114 and linkage with yoke 33, discussed below. Attached to base element 45 is a generally T-shaped finger interface 43, which in conjunction with base element 45 define two generally U-shaped openings, a forefinger groove 42 and a middle finger groove 44. The most distal surface portion of T-shaped finger interface 43 defines an actuating surface 41 that also accepts placement of fingers 382 and 384. Grooves 42 and 44 are sized to accept different sized fingers, a common variable as is evident depending upon the sex and size of the surgeon. In a first expression of the current embodiment, the size of grooves 42 and 44 are based on anthropic data for 5th percentile females through to 95th percentile males for finger size. In a second expression of the current embodiment, grooves 42 and 44 are tapered, whereby the dimension of each groove opening is larger than the dimension of base of each groove 42 and 44. This configuration advantageously allows fingers of varying size to nestle snuggly within each groove and minimize the clearance between the finger and walls of the grooves.

Figure 10:
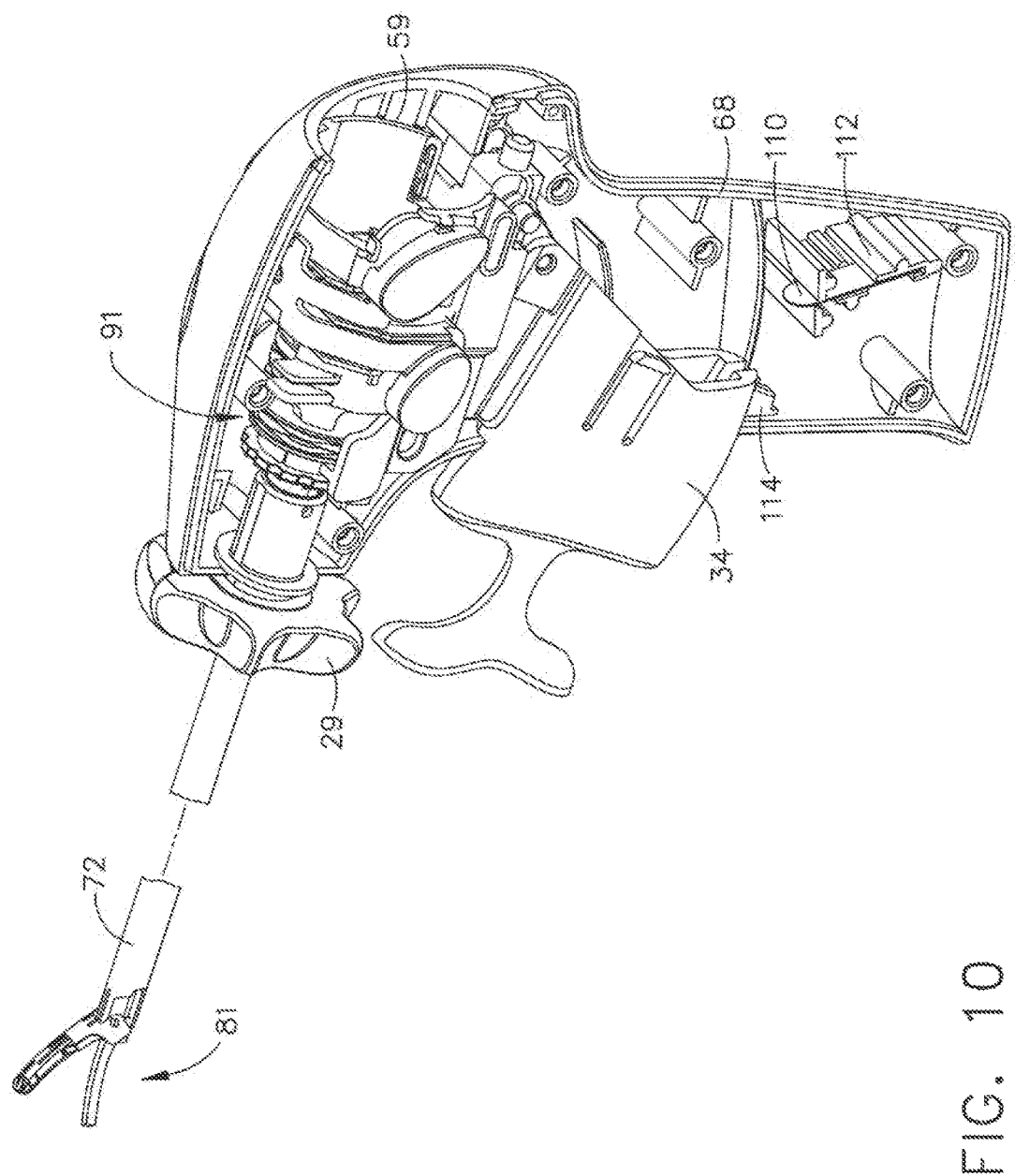
FIG. 10 is a perspective view of an ultrasonic surgical instrument with the trigger extended distally and the clamp arm in the open position.
Figure 11:
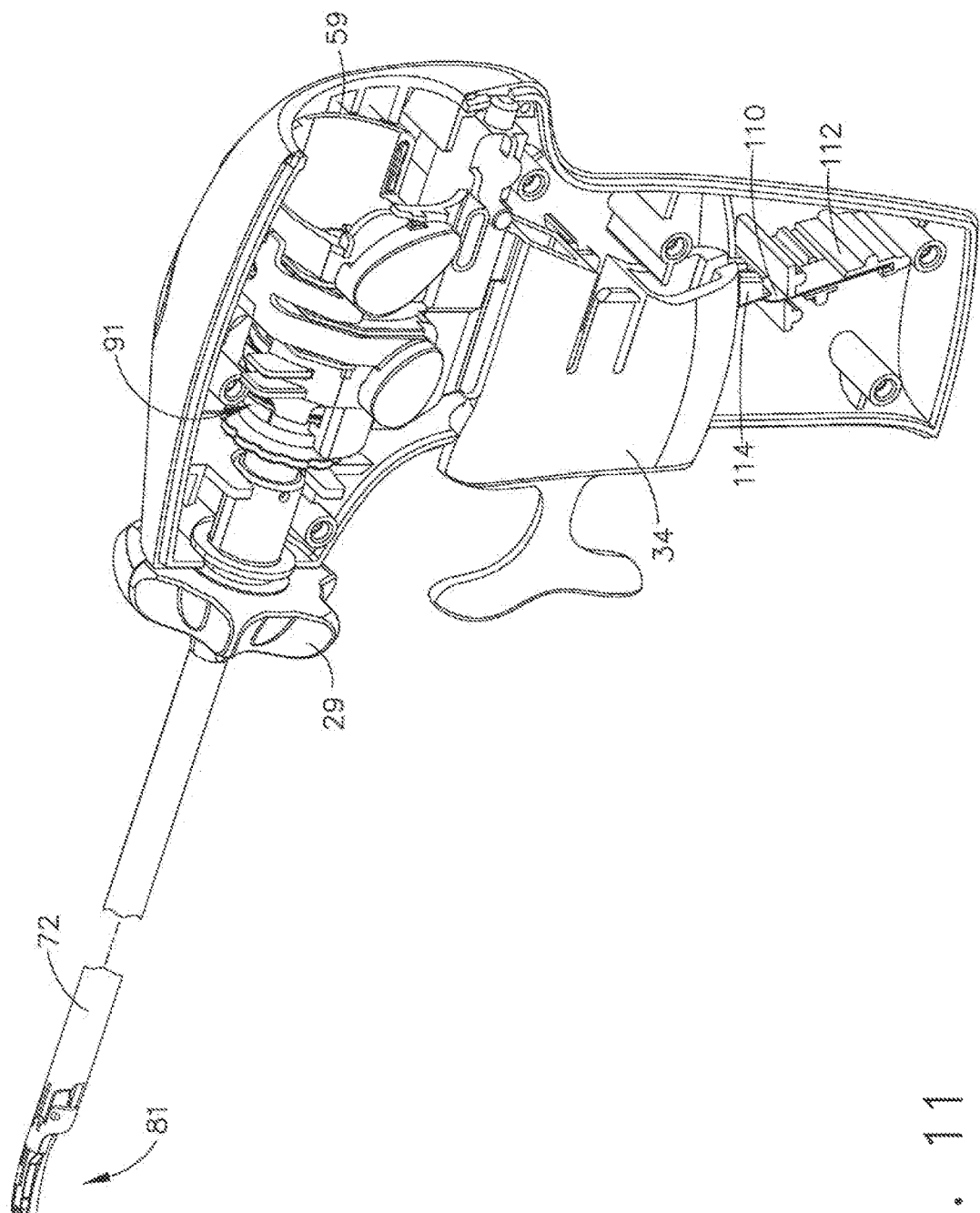
FIG. 11 is a perspective view of an ultrasonic surgical instrument with the trigger retracted proximally and the clamp arm in the closed position.

Referring now also to FIGS. 10 and 11, the clamp arm 56 is fully open relative to the blade 79 when trigger 34 is in its most distal position (FIG. 10). Fingers 382 and 384 may be placed within respective grooves 42 and 44 or alternatively on surface 41 to actuate trigger 34 through its arcuate travel designated by arrow 47. When trigger reaches its full proximal travel (when detent tab 114 engages detent spring 110), the clamp arm 56 is in its fully closed position relative to the blade 79 (FIG. 11). In order to reverse the trigger along its travel 47, fingers 382 and 384 engage grooves 42 and 44 and push trigger 34 distally to open the end effector. The clamp arm 56 is not biased open so the surgeon cannot control the opening of clamp arm 56 via surface 41.

Figure 18:
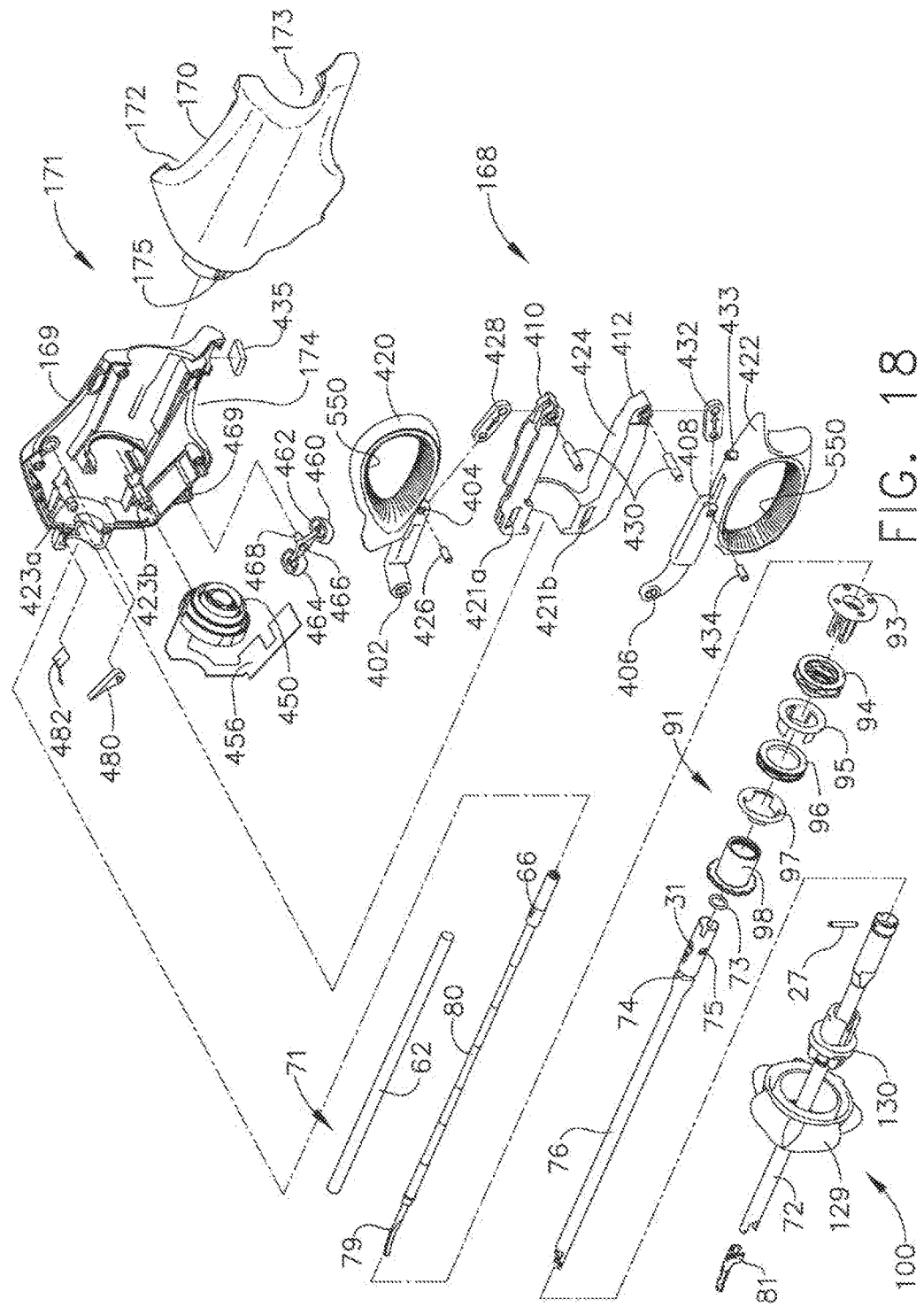
FIG. 18 is a perspective assembly view of a second embodiment of an ultrasonic surgical instrument in accordance with the present invention.

Referring now to FIG. 18, elements having similar reference numerals as shown in FIG. 2 have the similar function as already discussed. Particular attention is directed to an alternate handle assembly 168 for actuating the end effector 81. The handle assembly 168 includes two pivoting handle portions 420 and 422 coupled to a right shroud 169 and a left shroud 170.

The right shroud 169 is adapted to snap fit on the left shroud 170 via a plurality of inwardly facing prongs formed on the left shroud 170 to form housing 171. When the left shroud 170 is attached to the right shroud 169, a cavity is formed therebetween to accommodate various components that form the handle assembly 168 as further discussed below. Apertures 172 and 174 are also formed to accommodate thumb ring or handle portion 420 and finger ring or handle portion 422, which are located exterior of the left and right shrouds to the actuating linkage contained within the left and right shrouds. Aperture 173 is also formed at the proximal end of shrouds to accommodate transducer 50 (See FIG. 8*b*).

Handle assembly 168 includes a U-shaped yoke 424 slidably attachable within housings 169 and 170 via slots 421*a* and 421*b* and pins 423*a* and 423*b*, respectively. The distal end of handle 420 at hole 402 attaches to right shroud 169 and yoke via pin 423*a*, and the proximal end of handle 420 attaches to yoke 424 via link 428 attached to hole 404 via pin 426 and hole 410 via pin 430. The distal end of handle 422 at hole 406 attaches to right shroud 169 and yoke via pin 423*b*, and the proximal end of handle 422 attaches to yoke 424 via link 432 attached to hole 408 via pin 434 and hole 412 via pin 430. In practice as the handles 420 and 422 are moved away from housing 171 (for example, the surgeon's thumb cooperates with handle 420, and the surgeon's forefinger and middle finger cooperate with handle 422), end effector 81 moves away from blade 79 to form an open jaw (the open position), and as handles 420 and 422 are moved toward housing 171, end effector 81 rotates toward blade 79 to capture tissue (the closed position).

In one expression of the current embodiment, a detent spring 482 is supported within housing portion 171. A detent cam 480 rotates on yoke 168 and engages and snaps back detent spring 482 when handles 420 and 422 are in the fully closed position. Detent spring 482 is generally made of a flexible plastic that adequately deflects when it engages cam 480 thereby providing an audible signal to the surgeon that there is full end effector 81 closure. Advantageously, 480 strikes and deflects detent spring 482 when handles 420 and 422 are rotated from the full closure position and in the opposite direction thereby providing an audible signal to the surgeon that full closure of end effector 81 no longer exists.

Figure 24:
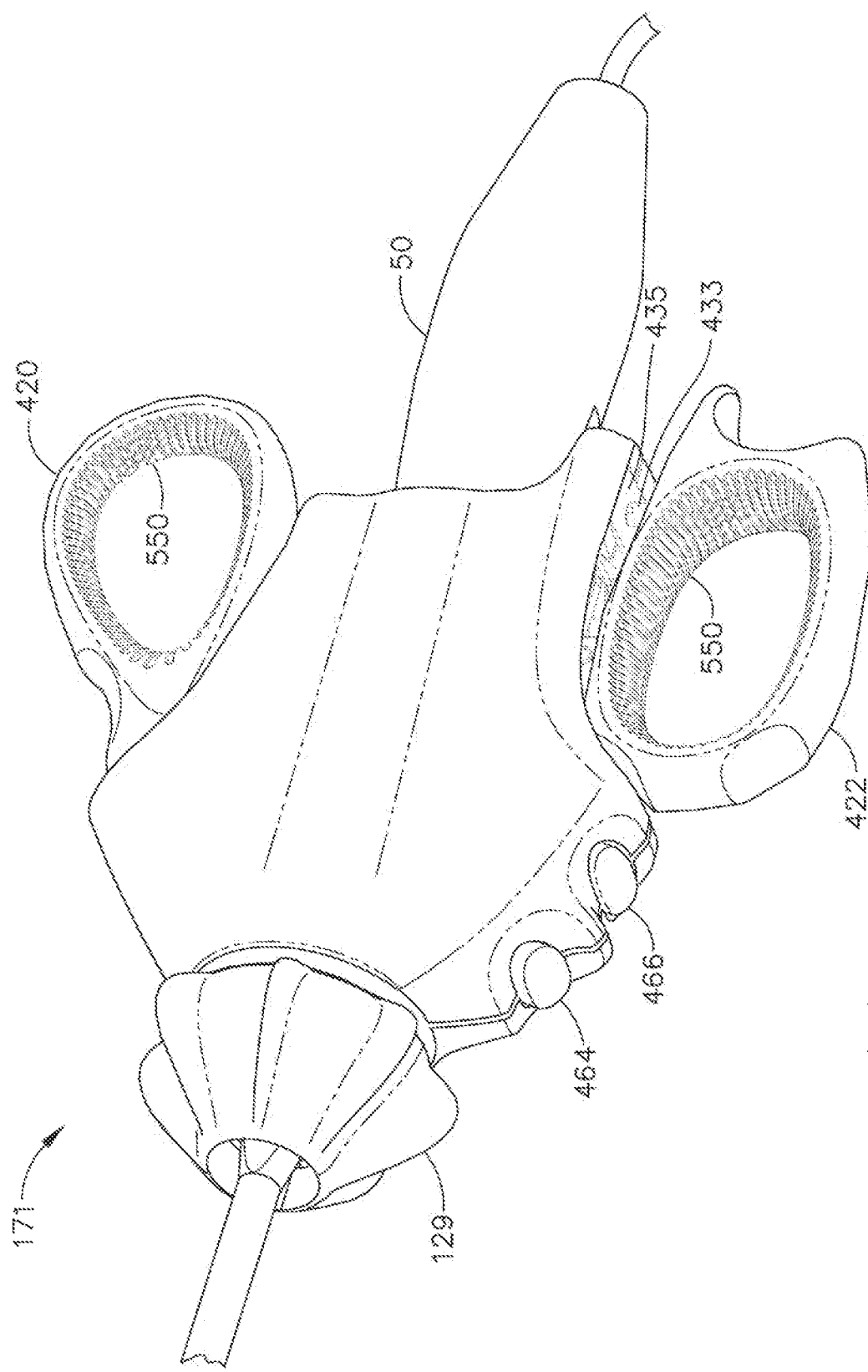
FIG. 24 is a perspective view of a surgical instrument in an alternate aspect of the invention.

Referring also now to FIG. 24, a second expression of the current embodiment is shown having an actuator post 433 attaches to handle 422 and engages a dome switch 435 covered by silicon rubber located on housing assembly 171. When handle 422 is fully closed, post 433 presses against the silicone which in turn transfers the force to the dome switch 435, allowing the switch to provide an audible and tactile feedback to the surgeon. In one embodiment post 433 is a cylinder having a diameter of 0.170 inches with a 0.070 inch slot in the middle. A preferred durometer for the silicon rubber material is 20 Shore A.

Figure 21:
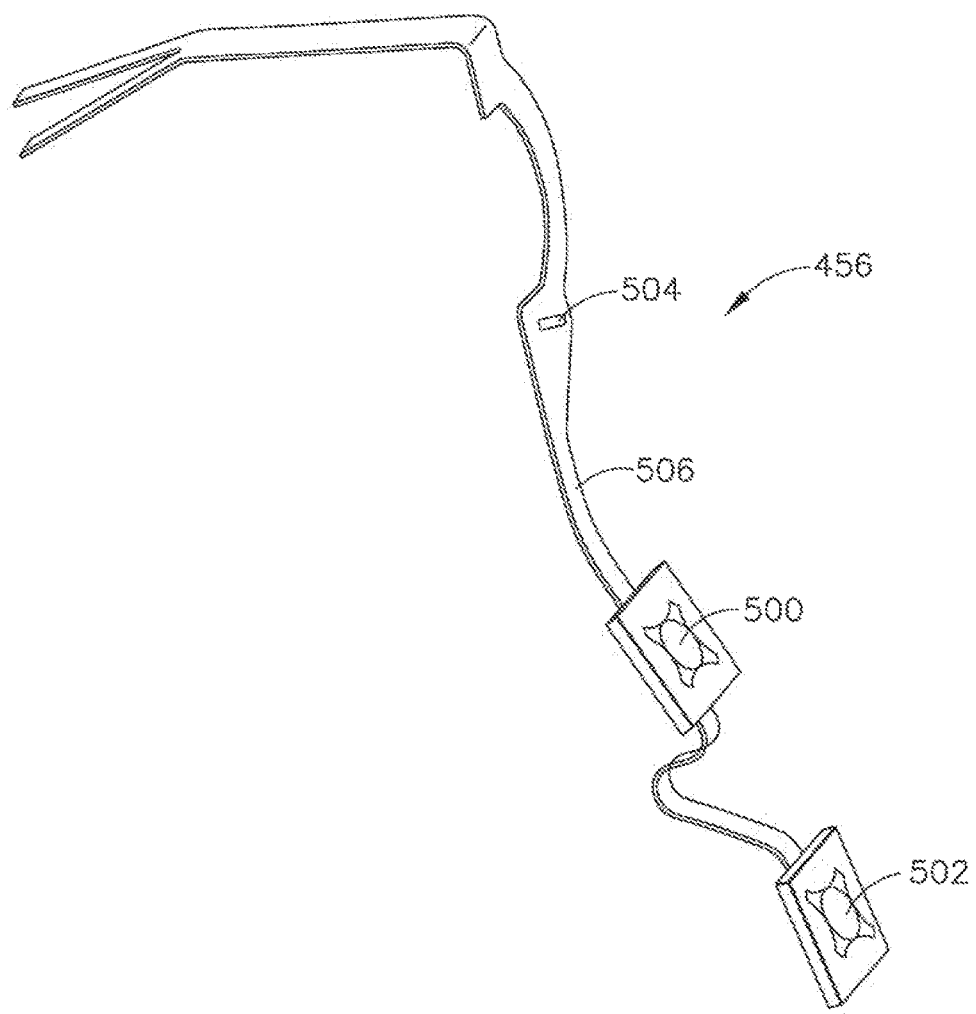
FIG. 21 is an exploded view of the flex circuit apparatus
Figure 22:
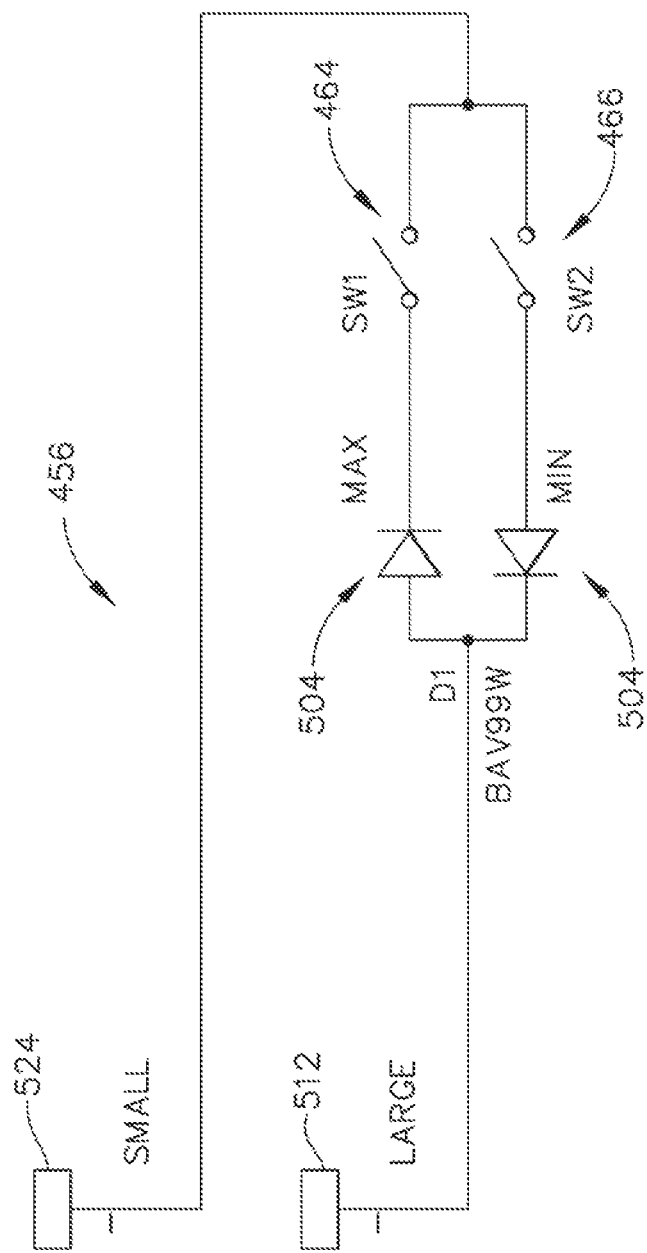
FIG. 22 is an electrical schematic of the flex circuit of FIG. 21
Figure 23:
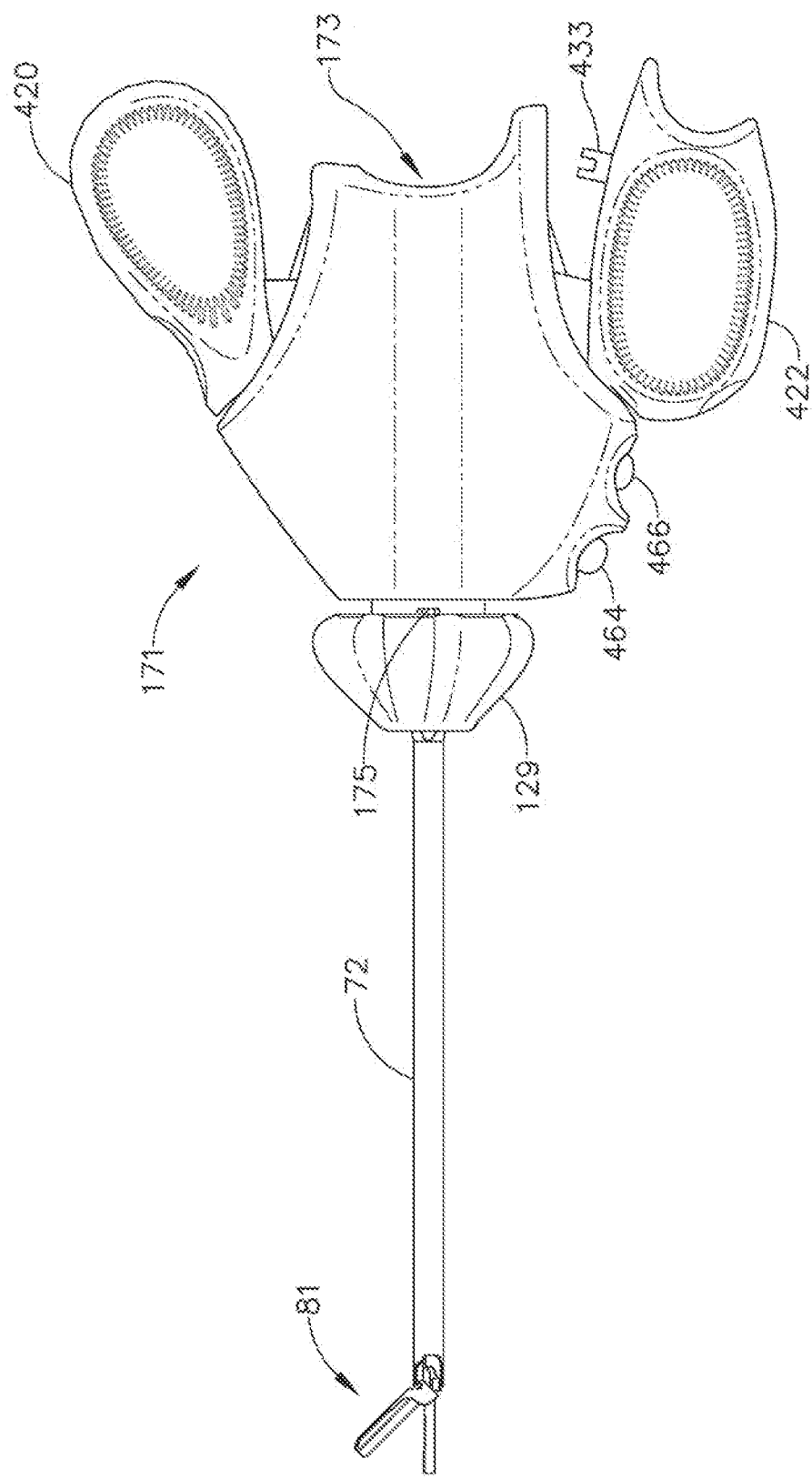
FIG. 23 is an elevation view of a surgical instrument in accordance with one aspect of the invention.

Referring also now to FIG. 23, also enclosed within housing 171 are connector 450, slip rings 452, 454, flex circuit 456 and rocker switch 462. Rocker switch 462 rotatably attaches to right shroud 169 via aperture 469 and switches 462 and 464 are positioned exterior housing 171 for access by the surgeon. Switches 462 and 464 are mechanically connected via a rocker arm 466 comprising a pivot post 468 which interfaces with aperture 469. In this configuration, switches 462 and 464 cannot be simultaneously depressed, which, if were the case, would provide an error message from generator 30. A flex circuit 456 provides for the electro-mechanical interface between switches 464 and 466 and the generator 30 via the transducer 50 (see FIG. 8b). Referring to FIG. 21, flex circuit 456 includes, at the distal end, two dome switches 500 and 502 that are mechanically actuated by depressing corresponding switches 464 and 466, respectively. Dome switches 500 and 502 are electrical contact switches, that when depressed provide an electrical signal to generator 30 as shown by the electrical wiring schematic of FIG. 22. Flex circuit 456 also comprises two diodes within a diode package 504, also illustrated in FIG. 22. Flex circuit 456 provides conductors, as is known to those in the art, that connect to slip ring conductors 452 and 454 via connector 450, which in turn provide electrical contact to ring conductors 400 and 410 (FIG. 8b), which in turn are connected to conductors in cable 32 that connect to generator 30.

Figure 19:
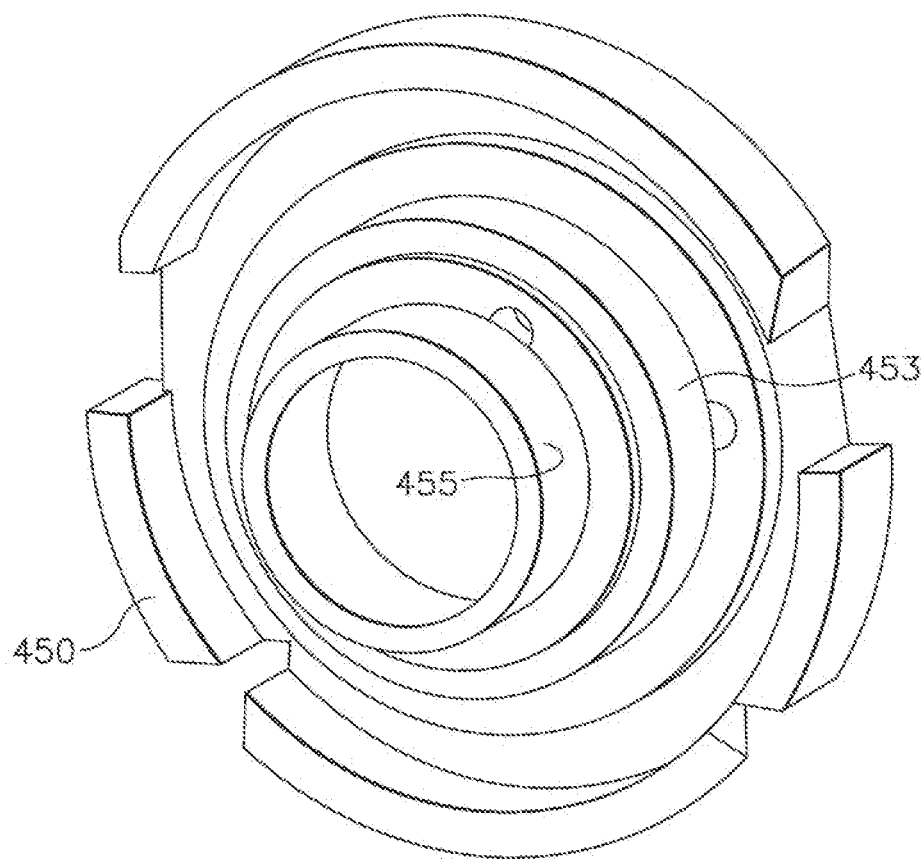
FIG. 19 is an exploded view of a handpiece connector.
Figure 20A:
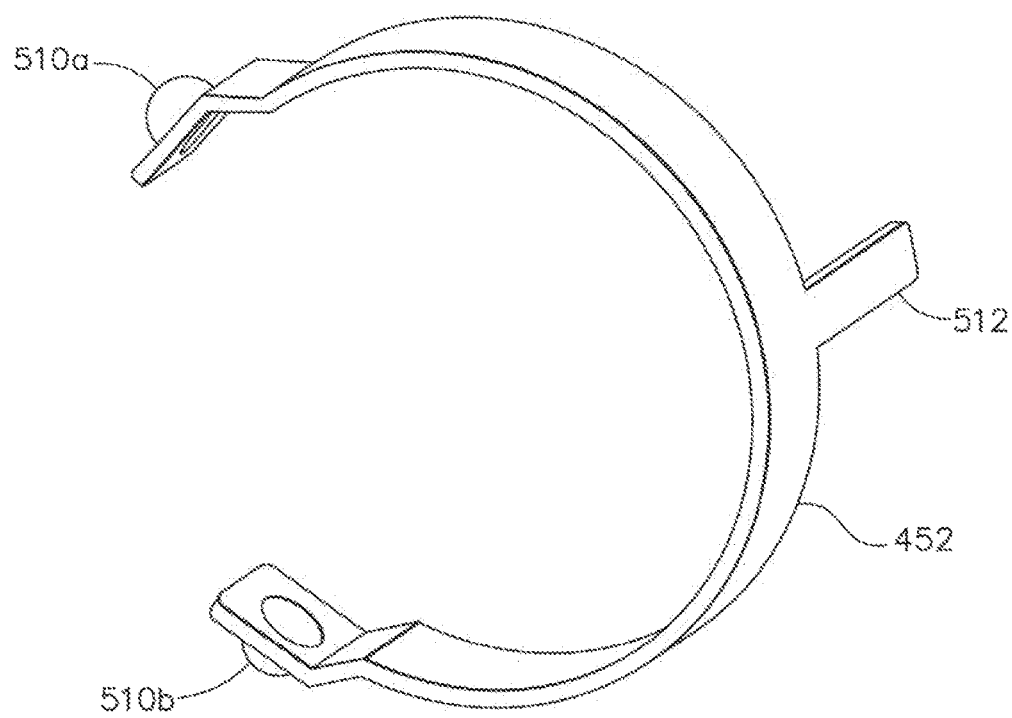
FIGS. 20a-b are exploded views of a large slip ring and a small slip ring, respectively.
Figure 20B:
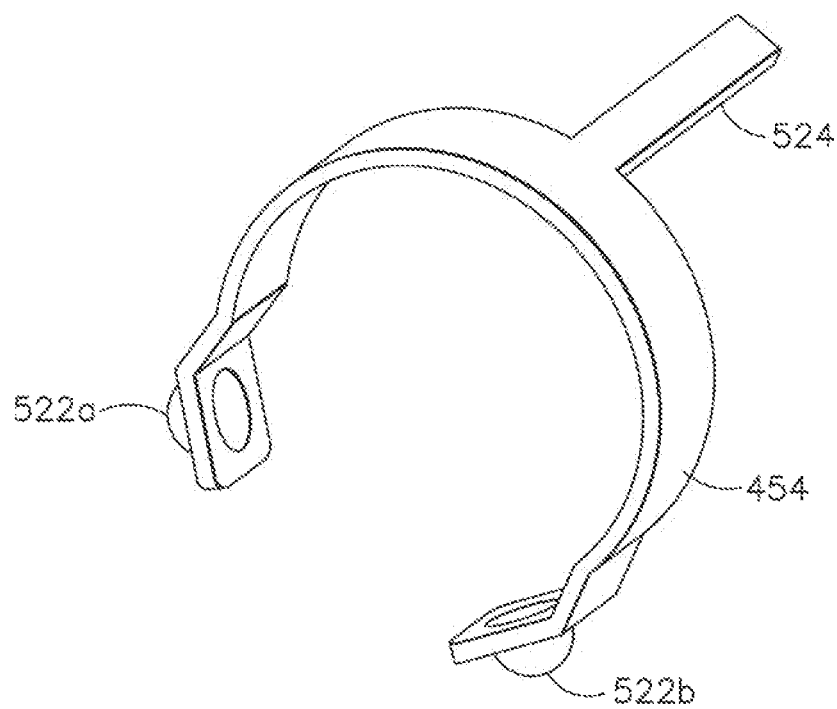

With particular reference now to FIGS. 19 and 20a-b, slip ring conductors 452 and 454 are generally open-ended O-shaped springs that slip onto mounting surfaces 453 and 455 of connector 450, respectively. Each spring slip-ring comprises two pressure point contacts (510a-b and 522a-b) that contact the respective ring conductor 400 and 410 of handpiece 50. The spring tension of the slip rings 452 and 454 cause positive contact between contacts 510a-b, 522a-b and conductors 400 and 410. It is evident that the slip-ring construction allows electrical contact to be made even as hand piece 50 may be rotated by the surgeon during use of the instrument. Posts 512 and 524 of the respective slip rings electrically connect to the respective conductor within flex circuit 456 to complete the electrical circuit as shown in FIG. 22.

Referring again to FIG. 18, rotation coupler 130 rotatably engages the distal end of right and left shrouds 169 and 170. Rotation knob 129 couples to rotational coupler 130, whereby two spring tabs 175 and 175a (not shown) provide an outward tension or force against the inner surface of rotation knob 129 to inhibit inadvertent rotation of end effector 81.

In an alternate expression of the invention, handles 420 and 422 have a soft-touch molded thermo plastic elastomer liner 550 on the inner surface of handles 420 and 422. Plastic liner 550 provides comfort to the surgeon and prevents finger and hand fatigue. Plastic liner 550 also provides an enhance gripping surface between the handles and the surgeon's thumb and fingers as opposed to the smooth plastic surface interface of the prior art. This is particularly advantageous for accepting multiple digit sizes of male and female surgeons and still providing a comfortable and positive gripping surface. Plastic liner 550 may be smooth or have contours molded onto the surface of liner 550, such as ribs, as illustrated in FIGS. 23 and 24. Other contours may be bumps, and peaks and valleys. Various other shapes and interfaces are within the scope of this invention as would be obvious to one skilled in the art. Plastic liner 550 is also useful on the interface between the surgeon's finger and trigger 34 (FIG. 12).

In one expression of the current embodiment, the soft-touch liner 550 has a durometer (hardness) rating from about 35 Shore A to about 75 Shore A, and more particularly from about 50 Shore A to about 60 Shore A. Such appropriate materials are available from LNP of Exton, Pa. (stock no. 8211-55 B100 GYO-826-3) and Advanced Elastomer Systems of Akron, Ohio (stock no. 8211-55B100).

The soft-touch material may also be useful to help the surgeon identify a particular feature of the instrument while the surgeon is focused on the operation at hand. For example, a "soft touch" having one contour interface may be placed on the "max" button, and a "soft touch" having a second contour interface may be place on the "min" button so the surgeon may easily recognize the presence of either button without having to lose focus of the surgical site. "Soft touch" may also be implemented on knobs 29 and 129 with contours to identify various rotation positions of end effector 81.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

We claim:

1. An ultrasonic clamp coagulator apparatus comprising:
a housing comprising an actuator;
an outer tube having a proximal end joined to the housing, and a distal end;
an ultrasonic waveguide having a proximal end and a distal end and further positioned within the outer tube;
an ultrasonically actuated blade attached to the distal end of the waveguide;
a clamp member pivotable with respect to the blade for clamping tissue between the clamp member and the blade; and
a force limiting mechanism comprising:
a first compression spring having a first spring constant, positioned between the actuator and the clamp arm wherein the first compression spring transfers a force at a first rate as a function of the motion of the actuator to pivotably move the clamp member toward the blade and;
a second compression spring having a second spring constant less than the first spring constant, wherein the second compression spring transfers a force at a second rate as a function of the motion of the actuator to pivotably move the clamp member toward the blade, where the second force rate is less than the first force rate, and wherein at least one of the first and second compression springs is precompressed to provide a preload less than the respective spring constant.

2. The ultrasonic clamp coagulator apparatus in accordance with claim 1, wherein the first compression spring has a spring constant greater than 100 pounds per inch.

3. The ultrasonic clamp coagulator apparatus in accordance with claim 2, wherein the first compression spring has a spring constant greater than 125 pounds per inch.

4. The ultrasonic clamp coagulator apparatus in accordance with claim 3, wherein the first compression spring has a spring constant of about 135 pounds per inch.

5. The ultrasonic clamp coagulator apparatus in accordance with claim 1, wherein the second compression spring has a spring constant greater than 25 pounds per inch.

6. The ultrasonic clamp coagulator apparatus in accordance with claim 5, wherein the second compression spring has a spring constant greater than 50 pounds per inch.

7. The ultrasonic clamp coagulator apparatus in accordance with claim 1, wherein the second compression spring has a spring constant of about 70 pounds per inch.

8. The ultrasonic clamp coagulator apparatus in accordance with claim 1, wherein the second compression spring is preloaded to a value to provide a required transaction force.

* * * * *